(12) United States Patent
Matar et al.

(10) Patent No.: US 9,827,331 B2
(45) Date of Patent: Nov. 28, 2017

(54) NUCLEIC ACID-LIPOPOLYMER COMPOSITIONS

(71) Applicant: CLSN Laboratories, Inc., Wilmington, DE (US)

(72) Inventors: Majed Matar, Madison, AL (US); Jason Fewell, Madison, AL (US); Danny H. Lewis, Hartselle, AL (US); Khursheed Anwer, Madison, AL (US)

(73) Assignee: CLSN Laboratories, Inc., Wlimington, DE (US)

( * ) Notice: Subject to any disclaimer, the term of this patent is extended or adjusted under 35 U.S.C. 154(b) by 0 days.

(21) Appl. No.: 14/866,493

(22) Filed: Sep. 25, 2015

(65) Prior Publication Data

US 2016/0243256 A1 Aug. 25, 2016

Related U.S. Application Data

(60) Division of application No. 13/605,462, filed on Sep. 6, 2012, now Pat. No. 9,144,546, which is a continuation of application No. 12/186,945, filed on Aug. 6, 2008, now abandoned.

(60) Provisional application No. 61/190,065, filed on Aug. 6, 2007.

(51) Int. Cl.

| A61K 48/00 | (2006.01) |
| A61K 38/20 | (2006.01) |
| A61K 47/48 | (2006.01) |
| A61K 9/19 | (2006.01) |
| C12N 15/113 | (2010.01) |
| C12N 5/00 | (2006.01) |
| A61K 9/00 | (2006.01) |
| A61K 9/127 | (2006.01) |
| A61K 31/70 | (2006.01) |
| A61K 47/26 | (2006.01) |
| A61K 47/36 | (2006.01) |
| A61K 47/38 | (2006.01) |
| C12N 15/11 | (2006.01) |
| C12N 15/88 | (2006.01) |
| A61K 47/60 | (2017.01) |
| A61K 47/54 | (2017.01) |
| A61K 47/59 | (2017.01) |
| A61K 47/64 | (2017.01) |
| A61K 38/00 | (2006.01) |

(52) U.S. Cl.
CPC ........ *A61K 48/0041* (2013.01); *A61K 9/0019* (2013.01); *A61K 9/1272* (2013.01); *A61K 9/19* (2013.01); *A61K 31/70* (2013.01); *A61K 38/208* (2013.01); *A61K 47/26* (2013.01); *A61K 47/36* (2013.01); *A61K 47/38* (2013.01); *A61K 47/554* (2017.08); *A61K 47/59* (2017.08); *A61K 47/60* (2017.08); *A61K 47/6455* (2017.08); *A61K 48/0075* (2013.01); *C12N 5/00* (2013.01); *C12N 15/111* (2013.01); *C12N 15/113* (2013.01); *C12N 15/88* (2013.01); *A61K 38/00* (2013.01); *C12N 2310/14* (2013.01); *C12N 2320/32* (2013.01); *C12N 2510/00* (2013.01)

(58) Field of Classification Search
None
See application file for complete search history.

(56) References Cited

U.S. PATENT DOCUMENTS

| 4,121,982 | A  | 10/1978 | Moriarty et al. |
| 5,283,185 | A  | 2/1994 | Epand et al. |
| 5,393,335 | A  | 2/1995 | Puckett et al. |
| 5,476,989 | A  | 12/1995 | Mimori et al. |
| 5,753,263 | A  | 5/1998 | Lishko et al. |
| 5,756,088 | A  | 5/1998 | Matsuura et al. |
| 5,945,400 | A  | 8/1999 | Scherman et al. |
| 5,955,415 | A  | 9/1999 | Gutierrez et al. |
| 6,177,274 | B1 | 1/2001 | Park et al. |
| 6,410,046 | B1 | 6/2002 | Lerner et al. |
| 6,696,038 | B1 | 2/2004 | Mahato et al. |
| 7,964,571 | B2 | 6/2011 | Fewell et al. |
| 8,057,821 | B2 | 11/2011 | Slobodkin et al. |
| 8,445,017 | B2 | 5/2013 | Slobodkin et al. |

(Continued)

FOREIGN PATENT DOCUMENTS

| CN | 1893924 A | 1/2007 |
| JP | 2003-524654 A | 8/2003 |

(Continued)

OTHER PUBLICATIONS

Aigner, A., et al., "Delivery of unmodified bioactive ribozymes by an RNA-stabilizing polyethylenimine (LMW-PEI) efficiently down-regulates gene expression," *Gene Therapy* 9(24):1700-1707, Nature Publishing Group, England (2002).

Anderson, W.F., "Human Gene Therapy," *Nature* 392(6679 Suppl):25-30, Macmillan Journals Ltd., England (1998).

Anderson, D.G., "Structure/Property Studies of Polymeric Gene Delivery Using a Library of Poly(β-amino esters)," *Molecular Therapy* 11(3):426-434, The American Society of Gene Therapy (2005).

Anwer, K., et al., "Cationic Lipid-based Delivery System for Systemic Cancer Gene Therapy," *Cancer Gene Ther* 7(8):1156-1164, Nature America, Inc., United States (2000).

(Continued)

*Primary Examiner* — Robert M Kelly

(74) *Attorney, Agent, or Firm* — Sterne, Kessler, Goldstein & Fox; Eric Steffe; Bonnie Nannenga-Combs

(57) ABSTRACT

Compositions, methods, and applications that increase the efficiency of nucleic acid transfection are provided. In one aspect, a pharmaceutical composition may include at least about 0.5 mg/ml concentration of a nucleic acid condensed with a cationic lipopolymer suspended in an isotonic solution, where the cationic lipopolymer includes a cationic polymer backbone having cholesterol and polyethylene glycol covalently attached thereto, and wherein the molar ratio of cholesterol to cationic polymer backbone is within a range of from about 0.1 to about 10, and the molar ratio of polyethylene glycol to cationic polymer backbone is within a range of from about 0.1 to about 10. The composition further may include a filler excipient.

28 Claims, 6 Drawing Sheets

(56) References Cited

U.S. PATENT DOCUMENTS

| | | | |
|---|---|---|---|
| 8,623,837 | B2 | 1/2014 | Fewell et al. |
| 9,144,546 | B2 | 9/2015 | Matar et al. |
| 9,468,687 | B2 | 10/2016 | Fewell et al. |
| 2003/0018002 | A1 | 1/2003 | Sagara |
| 2004/0048819 | A1 | 3/2004 | Simon et al. |
| 2004/0142474 | A1 | 7/2004 | Mahato et al. |
| 2004/0176282 | A1 | 9/2004 | Dalby et al. |
| 2007/0207966 | A1 | 9/2007 | Kim et al. |
| 2009/0042829 | A1 | 2/2009 | Matar et al. |
| 2013/0065942 | A1 | 3/2013 | Matar et al. |
| 2014/0186375 | A1 | 7/2014 | Fewell et al. |

FOREIGN PATENT DOCUMENTS

| | | | |
|---|---|---|---|
| JP | 2007-521247 A | 8/2007 | |
| WO | WO 96/21036 A2 | 7/1996 | |
| WO | WO 01/49324 A2 | 7/2001 | |
| WO | WO 01/64164 A2 | 9/2001 | |
| WO | WO 01/91789 A2 | 12/2001 | |
| WO | WO 02/22174 A1 | 3/2002 | |
| WO | WO 02/30468 A1 | 4/2002 | |
| WO | WO 03/008555 A2 | 1/2003 | |
| WO | WO 2005/060934 A1 | 7/2005 | |
| WO | WO 2009/021017 A2 | 2/2009 | |

OTHER PUBLICATIONS

Anwer, K., et al., "Recent Progress in Polymeric Gene Delivery Systems," *Crit Rev Ther Drug Carrier Syst* 20(4):249-293, Begell House, Inc., United States (2003).

Bennett, S.R.M., et al., "Help for Cytotoxic-T-Cell Responses is Mediated by CD40 Signalling," *Nature* 393(6684):478-480, Macmillan Publishers Ltd., England (1998).

Carrion, C., et al., "Preparation of long circulating immunoliposomes using PEG-cholesterol conjugates: effect of the spacer arm between PEG and cholesterol on liposomal characteristics," *Chem Phys Lipids* 113(1-2):97-110, Elsevier Science Ireland Ltd., Ireland (2001).

Chid, S.J., et al., "Tumor-targeted gene delivery via anti-HER2 antibody (trastuzumab, Herceptin®) conjugated polyethylenimine," *J Control Release* 97(2):357-369, Elsevier Science, B.V., Netherlands (2004).

Cohen, J., "IL-12 Deaths: Explanation and a Puzzle," *Science* 270(5238):908, American Association for the Advancement of Science, United States (1995).

Coleman, M., et al., "Nonviral Interferon α Gene Therapy Inhibits Growth of Established Tumors by Eliciting a Systemic Immune Response," *Hum Gene Ther* 9(15):2223-2230, Mary Ann Liebert, Inc., United States (1998).

Crystal, R.G., "Transfer of Genes to Humans: Early Lessons and Obstacles to Success," *Science* 270(5235):404-410, American Association for the Advancement of Science, United States (1995).

Davis, M.E., "Non-Viral Gene Delivery Systems," *Curr Opin Biotechnol* 13(2):128-131, Elsevier Science, Ltd., England (2002).

Deonarain, M.P., "Ligand-targeted receptor-mediated vectors for gene delivery," *Exp Opin Ther Patents* 8(1):53-69, Ashley Publications Ltd., England (1998).

Dow, S.W., et al., "Intravenous Cytokine Gene Delivery by Lipid-DNA Complexes Controls the Growth of Established Lung Metastases," *Hum Gene Ther* 10:2961-2972, Mary Ann Liebert, Inc., United States (1999).

Felgner, P.L., et al., "Lipofection: A Highly Efficient, Lipid-Mediated DNA-Transfection Procedure," *Proc Natl Acad Sci USA* 84:7413-7417, National Academy of Sciences, United States (1987).

Fewell, J.G., et al., "Synthesis and application of a non-viral gene delivery system for immunogene therapy of cancer," *Journal of Controlled Release* 109(1-3):288-298, Elsevier Science Publishers, Netherlands (2005).

Fidler, I.J., "Orthotopic implantation of human colon carcinomas into nude mice provides a valuable model for the biology and therapy of metastasis," *Cancer Metastasis Rev* 10(3):229-243, Kluwer Academic Publishers, Netherlands (1991).

Furgeson, D.Y., et al., "Tumor efficacy and biodistribution of linear polyethylenimine-cholesterol/DNA complexes," *Molecular Therapy* 9(6):837-845, The American Society of Gene Therapy, United States (2004).

Gao, X. and Huang, L., "A Novel Cationic Liposome Reagent for Efficient Transfection of Mammalian Cells," *Biochem Biophys Res Commun* 179(1):280-285, Academic Press, Inc., United States (1991).

Gerson, S.L., "MGMT: Its Role in Cancer Aetiology and Cancer Therapeutics," *Nat Rev Cancer* 4(4):296-307, Nature Publishing Group, England (2004).

Godbey, W.T., et al., "Poly(ethylenimine) and its role in gene delivery," *Journal of Controlled Release* 60(2-3):149-160, Elsevier Science B.V., Netherlands (1999).

Goverdhana, S., et al., "Regulatable Gene Expression Systems for Gene Therapy Applications: Progress and Future Challenges," *Mol Ther* 12(2):189-211, Academic Press, United States (2005).

Hambardzumyan, D., et al., "An update on mouse brain tumor models in cancer drug discovery," *Expert Opinion on Drug Discovery* 2(11):1435-1451, Informa UK Ltd., England (2007).

Han, S., et al., "Development of Biomaterials for Gene Therapy," *Mol Ther* 2(4):302-317, The American Society of Gene Therapy, United States (2000).

Heyes, J., et al., "Lipid Encapsulation Enables the Effective Systemic Delivery of Polyplex Plasmid DNA," *Molecular Therapy* 15(4):713-720, Academic Press, United States (2007).

Hong, K., et al., "Stabilization of cationic liposome-plasmid DNA complexes by polyamines and poly(ethylene glycol)-phospholipid conjugates for efficient in vivo gene delivery," *FEBS Lett* 400(2):233-237, Federation of European Biochemical Societies, Netherlands (1997).

Janat, et al., "Synergistic effects of local IL-12 gene therapy with a novel biodegradable paclitaxel delivery system," *Proc Am Soc Clin Oncol* 22:2 pages, American Society of Clinical Oncology, United States (2003) (Abstract 933).

Janát-Amsbury, M.M., et al., "Combination of local, nonviral IL12 gene therapy and systemic paclitaxel treatment in a metastatic breast cancer model," *Mol Ther* 9(6):829-836, The American Society of Gene Therapy, United States (2004).

Jia, S.F., et al., "Aerosol Gene Therapy with PEI:IL-12 Eradicates Osteosarcoma Lung Metastases," *Clin Cancer Res* 9(9):3462-3468, American Association for Cancer Research, United States (2003).

Kelland, L.R., "'Of mice and men: values and liabilities of the athymic nude mouse model in anticancer drug development," *Eur J Cancer* 40(6):827-836, Elsevier Ltd., England (2004).

Kerbel, R. S., "Human Tumor Xenografts as Predictive Preclinical Models for Anticancer Drug Activity in Humans," *Cancer Biol Ther* 2(4 Suppl 1):S134-139, Landes Bioscience, United States (2003).

Lee, M.J., et al., "Intraperitoneal gene delivery mediated by a novel cationic liposome in a peritoneal disseminated ovarian cancer model," *Gene Therapy* 9:859-866, Nature Publishing Group, England (2002).

Lenzi, R., et al., "Phase I Study of Intraperitoneal Recombinant Human Interleukin 12 in Patients with Müllerian Carcinoma, Gastrointestinal Primary Malignancies, and Mesothelioma," *Clin Cancer Res* 8(12):3686-3695, American Association for Cancer Research, United States (2002).

Lesage, D., et al., "Evaluation and optimization of DNA delivery into gliosarcoma 9L cells by a cholesterol-based cationic liposome," *Biochim Biophys Acta* 1564(20):393-402, Elsevier Science B.V., Netherlands (2002).

Li, D., et al., "Combination Nonviral Interleukin 2 and Interleukin 12 Gene Therapy for Head and Neck Squamous Cell Carcinoma," *Arch Otolaryngol Head Neck Surg* 127(11):1319-1324, American Medical Association, United States (2001).

Li, D., et al., "Interleukin 2 Gene Transfer Prevents NKG2D Suppression and Enhances Antitumor Efficacy in Combination with Cisplatin for Head and Neck Squamous Cell Cancer," *Cancer Res* 62(14):4023-4028, American Association for Cancer Research, United States (2002).

Li, S.D. and Huang, L., "Gene therapy progress and prospects: non-viral gene therapy by systemic delivery," *Gene Ther* 13(18):1313-1319, Nature Publishing Group, England (2006).

(56) References Cited

OTHER PUBLICATIONS

Liu, Y., et al., "Cationic Liposome-mediated Intravenous Gene Delivery," *J Biol Chem* 270(42):24864-24870, The American Society for Biochemistry and Molecular Biology, Inc., United States (1995).

Mahato, R.I., et al.,"Intratumoral delivery of p2CMVmIL-12 using water-soluble lipopolymers," *Mol Ther* 4(2):130-138, The American Society of Gene Therapy, United States (2001).

Maheshwari, A., et al., "Biodegradable Polymer-based Interleukin-12 Gene Delivery: Role of Induced Cytokines, Tumor Infiltrating Cells and Nitric Oxide in Anti-Tumor Activity," *Gene Ther* 9(16):1075-1084, Macmillan Publishers Ltd., England (2002).

Maruyama-Tabata, H., et al., "Effective Suicide Gene Therapy in Vivo by EBV-based Plasmid Vector Coupled with Polyamidoamine Dendrimer," *Gene Ther* 7(1):53-60, Macmillan Publishers Ltd., England (2000).

Mendiratta, S.K., et al., "Combination of Interleukin 12 and Interferon α Gene Therapy Induces a Synergistic Antitumor Response against Colon and Renal Cell Carcinoma," *Hum Gene Ther* 11(13):1851-1862, Mary Ann Liebert, Inc., United States (2000).

Merdan, T., et al., "Pegylated polyethylenimine-Fab' antibody fragment conjugates for targeted gene delivery to human ovarian carcinoma cells," *Bioconjug Chem* 14(5):989-996, American Chemical Society, United States (2003).

Meyer, O., et al., "Cationic Liposomes Coated with Polyethylene Glycol As Carriers for Oligonucleotides," *J Biol Chem* 273(25):15621-15627, American Society for Biochemistry and Molecular Biology, United States (1998).

Miller, N. and Vile, R., "Targeted vectors for gene therapy," *FASEB J* 9(2):190-199, FASEB, United States (1995).

Mosmann, T., "Rapid Colorimetric Assay for Cellular Growth and Survival: Application to Proliferation and Cytotoxicity Assays," *J Immunol Methods* 65(1-2):55-63, Elsevier Science Publishers B.V., Netherlands (1983).

Nabel, E.G., et al., "Gene Transfer In Vivo With DNA-Liposome Complexes: lack of autoimmunity and gonadal localization," *Human Gene Therapy* 3(6):649-656, Mary Ann Liebert, Inc., Publishers, United States (1992).

Nakanishi, H., et al., "Nonviral Genetic Transfer of Fas Ligand Induced Significant Growth, Suppression and Apoptotic Tumor Cell Death in Prostate Cancer In Vivo," *Gene Ther* 10(5):434-442, Nature Publishing Group, England (2003).

Ogris, M., et al., "PEGylated DNA/transferrin-PEI complexes: reduced interaction with blood components, extended circulation in blood and potential for systemic gene delivery," *Gene Therapy* 6(4):595-605, Stockton Press, England (1999).

Ogris, M., et al., "Tumor-targeted gene therapy: strategies for the preparation of ligand-polyethylene glycol-polyethyleniminie/DNA complexes," *J Control Release* 91(1-2):173-181, Elsevier Science B.V., Netherlands (2003).

Ohlfest, J.R., et al., "Nonviral Vectors for Cancer Gene Therapy: Prospects for Integrating Vectors and Combination Therapies," *Curr Gene Ther* 5(6):629-641, Bentham Science Publishers Ltd., Netherlands (2005).

Oshikawa, et al., *Journal of Clinical and Experimental Medicine* (*Syuukann Igaku no Ayumi*) 188(7):768-769 (1999).

Prieto, J., et al., "Gene therapy of liver diseases," *Expert Opin Biol Ther* 4(7):1073-1091, Ashley Publications Ltd., England (2004).

Ridge, J.P., et al., "A Conditioned Dendritic Cell Can be a Temporal Bridge Between a CD4+ T-helper and a T-Killer Cell," *Nature* 393(6684):474-478, Macmillan Publishers Ltd., England (1998).

Robertson, M.J. and Ritz, J., "Interleukin 12: Basic Biology and Potential Applications in Cancer Treatment" *Oncologist* 1(1 & 2):88-97, AlphaMed Press, United States (1996).

Roth, C.M. and Sundaram, S., "Engineering Synthetic Vectors for Improved DNA Delivery: Insights from Intracellular Pathways," *Annu Rev Biomed Eng* 6:397-426, Annual Reviews, United States (2004).

Salem, M.L., et al., "Novel nonviral delivery approaches for interleukin-12 protein and gene systems: curbing toxicity and enhancing adjuvant activity," *J Interferon Cytokine Res* 26(9):593-608, Mary Ann Liebert, Inc., United States (2006).

Sarmiento, U.M., et al., "Biologic Effects of Recombinant Human Interleukin-12 in Squirrel Monkeys (*Sciureus saimiri*)," *Lab Invest* 71(6):862-873, The United States and Canadian Academy of Pathology, Inc., United States (1994).

Schoenberger, S.P., et al., "T-cell help for cytotoxic T lymphocytes is mediated by CD40-CD40L interactions," *Nature* 393(6684):480-483, Macmillan Publishers Ltd., England (1998).

Schuh, T., et al., "DNA-Based Vaccine Against La Crosse Virus: Protective Immune Response Mediated by Neutralizing Antibodies and CD4+T Cells," *Hum Gene Ther* 10(10):1649-1658, Mary Ann Liebert, Inc., United States (1999).

Tare, N.S., et al., "Administration of Recombinant Interleukin-12 to Mice Suppresses Hematopoiesis in the Bone Marrow but Enhances Hematopoiesis in the Spleen," *J Interferon Cytokine Res* 15(4):377-383, Mary Ann Liebert, Inc., United States (1995).

Teicher, B.A., et al., "Optimal Scheduling of Interleukin 12 and Chemotherapy in the Murine MB-49 Bladder Carcinoma and B16 Melanoma," *Clin Cancer Res* 3(9):1661-1667, American Association for Cancer Research, United States (1997).

Tsung, K., et al., "Immune Response Against Large Tumors Eradicated by Treatment with Cyclophosphamide and IL-12," *J Immunol* 160(3):1369-1377, American Association of Immunologists, United States (1998).

Urushizaki, Antibiotics & Chemotherapy (Kagaku Ryouhou no Ryouiki), vol. 10, No. 6, 1031-1037 (1994).

Verma, I.M. and Somia, N., "Gene therapy—promises, problems, and prospects," *Nature* 389(6648): 239-242, Macmillan Journals Ltd., England (1997).

Voskoglou-Nomikos, T., et al., "Clinical Predictive Value of the in Vitro Cell Line, Human Xenograft, and Mouse Allograft Preclinical Cancer Models," *Clin Cancer Res* 9(11):4227-4239, American Association for Cancer Research, United States (2003).

Wei, M.Q., et al., "Sustained Gene Expression in Transplanted Skin Fibroblasts in Rats," *Gene Ther* 6(5):840-844, Stockton Press, England (1999).

Yockman, J.W., et al., "Tumor Regression by Repeated Intratumoral Delivery of Water Soluble Lipopolymers/p2CMVIiL-12 Complexes," *Journal of Controlled Release* 87(1-3):177-186, Elsevier Science B.V., Netherlands (2003).

Youssef, E.A., et al., "Enhancing Myocardial Plasmid Expression by Retrograde Coronary Venous Delivery," *Catheterization and Cardiovascular Interventions* 65(4):528-534, Wiley-Liss, Inc., United States (2005).

Zagozdzon, R., et al., "Effective Chemo-Immunotherapy of L1210 Leukemia In Vivo Using Interleukin-12 Combined with Doxorubicin but not with Cyclophosphamide Paclitaxel or Cisplatin," *Int J Cancer* 77(5):720-727, Wiley-Liss, Inc., United States (1998).

Zagozdzon, R., et al., "The Potentiated Antileukemic Effects of Doxorubicin and Interleukin-12 Combination are Not Dependent on Nitric Oxide Production," *Cancer Lett* 147(1-2):67-75, Elsevier Science Ireland Ltd., Ireland (1999).

International Preliminary Report on Patentability for International Application No. PCT/US2008/072306, European Patent Office, Netherlands, dated Feb. 9, 2010, 9 pages.

International Search Report with Written Opinion for International Application No. PCT/US2008/072306, European Patent Office, Netherlands, dated Mar. 13, 2009, 12 pages.

Brus, C., et al., "Stabilization of oligonucleotide-polyethylenimine complexes by freeze-drying: physicochemical and biological characterization," *Journal of Controlled Release* 95:119-131, Elsevier BV, The Netherlands (2004).

Duguid, J.G., et al., "A Physicochemical Approach for Predicting the Effectiveness of Peptide-Based Gene Delivery Systems for Use in Plasmid-Based Gene Therapy," *Biophysical Journal* 74:2802-2814, Biophysical Society, United States (1998).

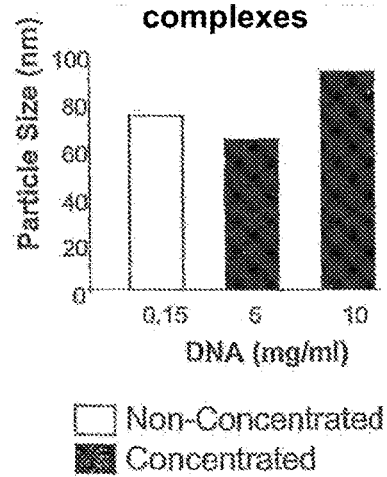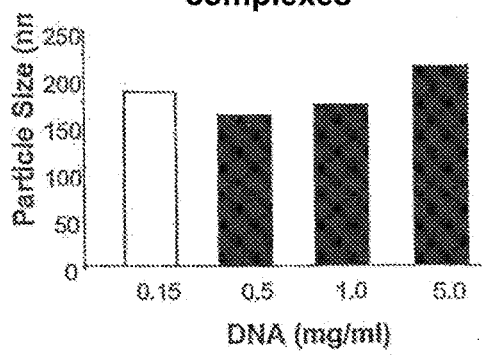
FIG. 2A: IL-12 plasmid-polymer complexes
FIG. 2B: Luciferase plasmid-polmer complexes
☐ Non-Concentrated
▩ Concentrated
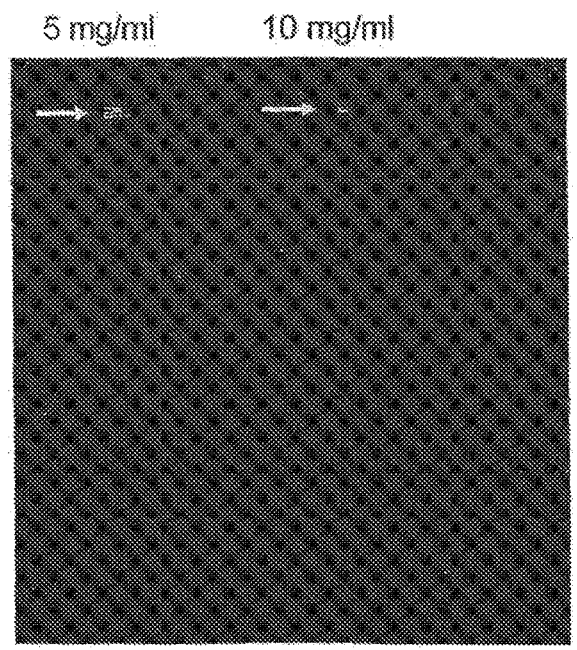
FIG. 3

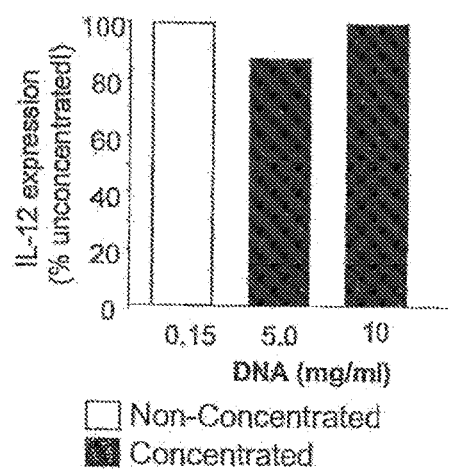
FIG. 4A: IL-12 plasmid-polymer complexes
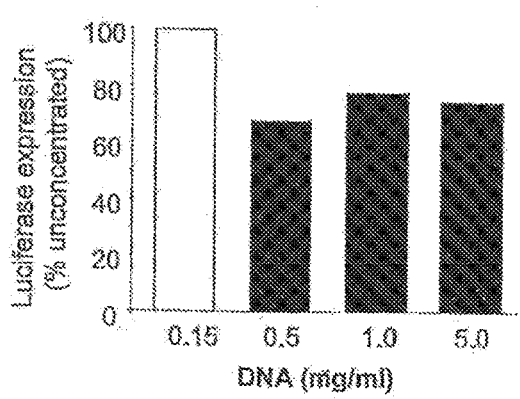
FIG. 4B: Luciferase plasmid-polmer complexes
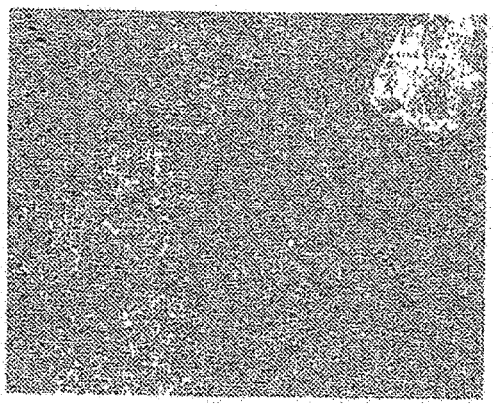
FIG. 5A: Control
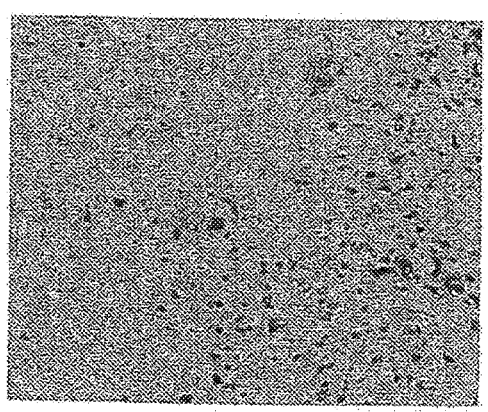
FIG. 5B: IL-12 Complexes

NUCLEIC ACID-LIPOPOLYMER COMPOSITIONS

CROSS-REFERENCE TO RELATED APPLICATIONS

This application is a divisional of U.S. application Ser. No. 13/605,462, filed Sep. 6, 2012, now granted U.S. Pat. No. 9,144,546 which is a continuation of U.S. application Ser. No. 12/186,945, filed Aug. 6, 2008, now abandoned, which claims priority to U.S. Provisional Application No. 61/190,065, filed Aug. 6, 2007, each of which is incorporated herein by reference in its entirety.

FIELD OF THE INVENTION

The invention relates to concentrated and stable formulations comprising nucleic acid and lipopolymer and to compositions, methods of preparation, and applications thereof. Accordingly, this invention involves the fields of molecular biology and biochemistry.

BACKGROUND OF THE INVENTION

Synthetic gene delivery vectors have considerable advantage over viral vectors due to better safety compliance, simple chemistry, and cost-effective manufacturing. However, due to low transfection efficiency of the synthetic vectors as compared to that of the viral vectors, most of the development in synthetic gene delivery systems has focused on improving delivery efficiency. Consequently, little attention has been given to the pharmaceutical development of synthetic delivery systems, although problems have been identified in formulation stability, scale up, and dosing flexibility. Pharmaceuticals containing DNA that self-assembles into nanoparticles often exhibit poor stability, particularly when the formulation is an aqueous suspension. In such formulations, DNA with synthetic vectors will typically aggregate over time, especially at concentrations required for optimal dosing in a clinical setting. Such formulations are often difficult to prepare at DNA concentrations >0.3 mg/ml, which limits their commercial applications, especially for local delivery where volume constraints would limit flexible dosing. DNA aggregation reduces or eliminates the activity of the DNA and therefore makes the composition unsuitable for use in treatment.

This physical instability is one of the underlying reasons for loss of transfection activity. Manifestation of particle rupture or fusion due to high curvature of the lipid bilayer or physical dissociation of lipid from DNA have also been postulated as potential underlying reasons for poor stability and aggregation of cationic lipid based gene delivery complexes. Chemical modification such as oxidative hydrolysis of the delivery vectors may also contribute to particle instability.

Because of poor stability, the early clinical trials required that DNA formulations be prepared by the bedside. Not having the ability to prepare and store the clinical product at concentrations required for optimal dosing is a major obstacle in the broad clinical practice and commercialization of the non-viral DNA products. This would require physicians training on drug formulation and pose on-site quality control measures.

Freeze-drying is a useful method for improving long-term stability of a number of drug pharmaceuticals. However, this process is not normally suitable for drying DNA complexes with synthetic vectors as it tends to alter their physicochemical properties and results in aggregation and loss of transfection upon reconstitution.

Several approaches have been attempted to prevent formulation aggregation and damage during lyophilization. In some cases, lyophilization of DNA complexes in the presence of a cryoprotectant such as low molecular weight sugars, dextrans, and polyethylene glycol may provide better stability to the product, but that approach does not appear to improve dosing flexibility. Addition of sugars is often the most commonly used approach for this purpose. Many of the test sugars have been found to prevent formulation damage and particle aggregation to some extent, but the quality of this effect varies with the type of sugar and the delivery vector used.

Although lyophilization provides some improvement in formulation shelf life, the conditions required to produce lyophilized DNA products allow for only limited pharmaceutical applications. Even with the most effective lyoprotectant sugars, a very high sugar/DNA molar ratio (typically greater than 1000:1) is required for stability. As a result, the lyophilized product often must be diluted by a very large factor to obtain an isotonic formulation, which results in a drop in the final DNA concentration to the pre-lyophilized DNA concentration. For many cationic carriers the final DNA concentration may typically be about 0.1-0.2 mg/ml, and often below 0.1 mg/ml. Although low concentration formulations are sufficient for in vitro studies, their clinical application may be limited due to high volume requirement for optimal dosing. For example, at the optimal sugar concentration needed for stability, a 1 mg dose of DNA may need to be diluted in 5-10 ml to maintain isotonicity, which is too large a volume for local in vivo administration. This pharmaceutical limitation, prohibitive of flexible dosing, is one of the principal contributors to suboptimal efficacy of synthetic gene delivery systems in human clinical trials and warrants the need for more concentrated DNA formulations that are stable and biologically active.

SUMMARY OF THE INVENTION

The invention provides compositions that demonstrate unexpected stability at high nucleic acid concentration and that increase the efficiency and dosing flexibility of nucleic acid transfection. The compositions described herein can efficiently be lyophilized and reconstituted to various nucleic acid concentrations, including high nucleic acid concentrations, without losing biological activity or aggregation of nucleic acid.

In one aspect, the invention provides compositions, preferably pharmaceutical compositions, comprising a mixture of a cationic lipopolymer and at least about 0.5 mg/ml of a nucleic acid, where the mixture is suspended in an aqueous solution. The cationic lipopolymer comprises a cationic polymer backbone having cholesterol and polyethylene glycol groups independently covalently attached thereto. The molar ratio of cholesterol to cationic polymer backbone is within a range of from about 0.1 to about 10, and the molar ratio of polyethylene glycol to cationic polymer backbone is within a range of from about 0.1 to about 10. The composition further may include a filler excipient. In certain aspects, the mixture of nucleic acid and lipopolymer forms a complex. In certain aspects the composition comprises condensed nucleic acid. The amount of nucleic acid that is condensed will generally depend on the compositional makeup of the nucleic acid and the conditions under which composition is prepared.

The invention also provides methods of making the compositions described above.

In another aspect, the invention provides lyophilized compositions of a nucleic acid and a lipopolymer. A lyophilized composition, preferably a lyophilized pharmaceutical composition, of the invention comprises a mixture of a filler excipient, a nucleic acid condensed, and a cationic lipopolymer. As noted above, the cationic lipopolymer includes a cationic polymer backbone having cholesterol and polyethylene glycol covalently attached thereto, and wherein the molar ratio of cholesterol to cationic polymer backbone is within a range of from about 0.1 to about 10, and the molar ratio of polyethylene glycol to cationic polymer backbone is within a range of from about 0.1 to about 10.

The invention additionally provides methods for using the compositions described herein in the treatment of diseases and/or disorders by, e.g., transfecting various cells and tissues.

BRIEF DESCRIPTION OF THE DRAWINGS

FIG. 2A and FIG. 2B show graphs of particle size of nucleic acids in concentrated and non-concentrated states.

FIG. 3 shows results of an electrophoretic experiment to show nucleic acid condensation.

FIG. 4A and FIG. 4B show graphs of transfection activity according to a further embodiment of the invention.

FIG. 5A and FIG. 5B are photographs of neural slices showing the results of treatment with lipopolymer with and without IL-12.

DETAILED DESCRIPTION

Figure 1:
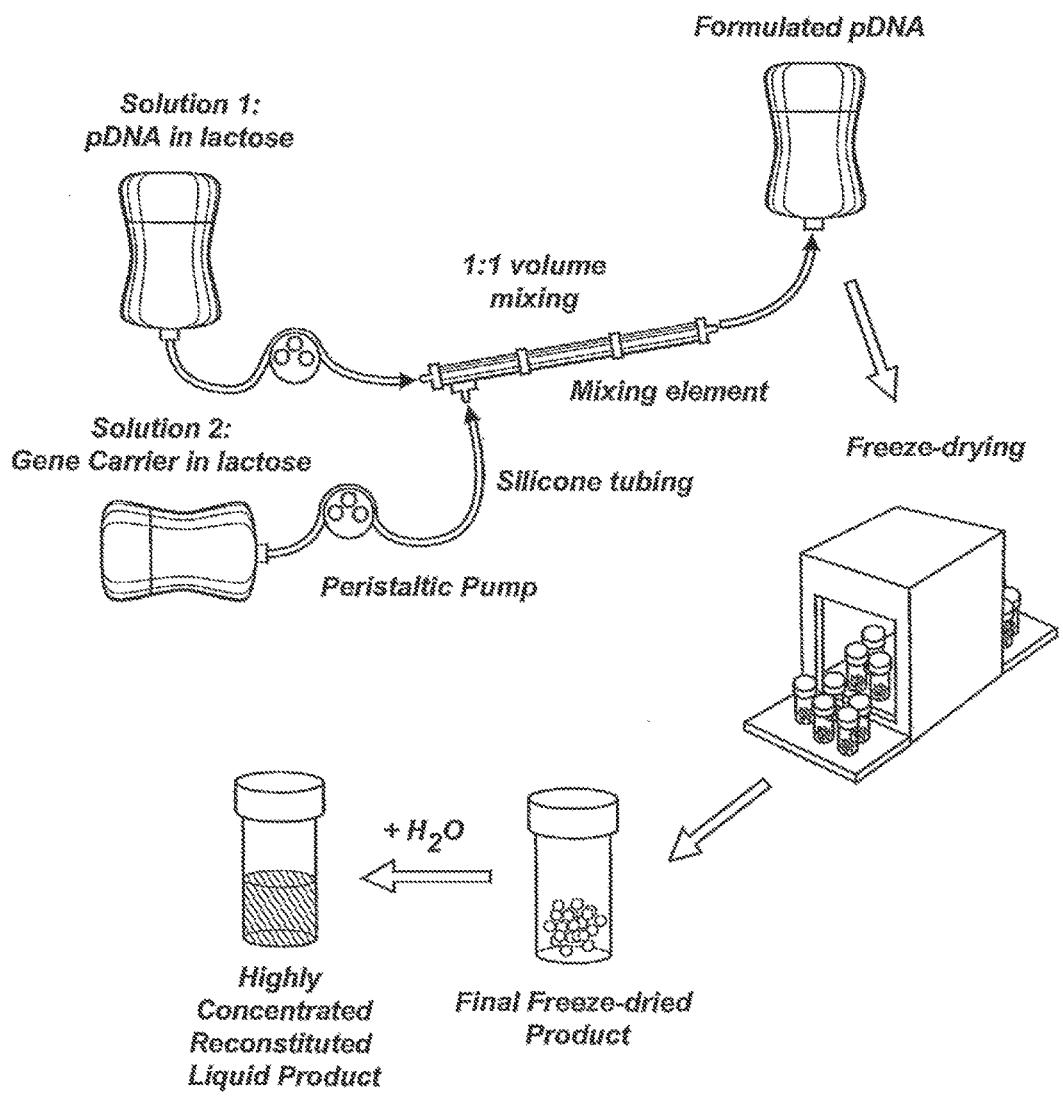
FIG. 1 is a schematic of a manufacturing process of the invention.

Before the invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting since the scope of the invention will be limited only by the appended claims and equivalents thereof.

It must be noted that, as used in this specification and the appended claims, the singular forms "a," "an," and "the" include plural referents unless the context clearly dictates otherwise.

As used herein, the terms "condensed nucleic acid" and "partially condensed nucleic acid" are used to refer to a nucleic acid that has been contacted with a cationic lipopolymer of the invention. In certain aspects, the condensed nucleic acid remains in contact with the cationic lipopolymer. Condensed nucleic acids typically occupy a significantly smaller volume than non-condensed nucleic acids. It is recognized, however, that the amount of condensed nucleic acid may vary with local environment (e.g., lipid as opposed to aqueous environment). In various aspects of the invention, the condensed nucleic acids are those in nanoparticles of nucleic acid and cationic lipopolymer having a size of from about 50 nm to about 300 nm, more preferably from about 50-200, and even more preferably from about 50-150 nm. "Partially condensed nucleic acid" refers to a nucleic acid that has been contacted with a cationic lipopolymer of the invention wherein the nucleic acid is less than fully condensed, yet still occupy a significantly smaller volume than non-condensed nucleic acid.

As used herein, the term "complex" means nucleic acid that is associated with lipopolymer, preferably, cationic lipopolymer. A complex that includes condensed nucleic acid and cationic lipopolymer will typically exist as particles, preferably as nanoparticle.

As used herein, the terms "transfecting" and "transfection" refer to the transportation of nucleic acids from the environment external to a cell to the internal cellular environment, with particular reference to the cytoplasm and/or cell nucleus. Without being bound by any particular theory, it is to be understood that nucleic acids may be delivered to cells either after being encapsulated within or adhering to one or more cationic polymer/nucleic acid complexes or being entrained therewith. Particular transfecting instances deliver a nucleic acid to a cell nucleus.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals.

As used herein, "composition" refers to a mixture of two or more compounds, elements, or molecules. In some aspects the term "composition" may be used to refer to a mixture of a nucleic acid and a delivery system.

As used herein, "N:P ratio" refers to the molar ratio of amine nitrogens in the functionalized cationic lipopolymer and the phosphate groups in the nucleic acid.

As used herein, "physicochemical properties" refers to various properties such as, without limitation, particle size and surface charge of nucleic acid complexes with a cationic polymer, pH and osmolarity of the particle solution, etc.

As used herein, the terms "administration," "administering," and "delivering" refer to the manner in which a composition is presented to a subject. Administration can be accomplished by various art-known routes such as oral, parenteral, transdermal, inhalation, implantation, etc. Thus, an oral administration can be achieved by swallowing, chewing, sucking of an oral dosage form comprising the composition. Parenteral administration can be achieved by injecting a composition intravenously, intra-arterially, intramuscularly, intraarticularly, intrathecally, intraperitoneally, subcutaneously, etc. Injectables for such use can be prepared in conventional forms, either as a liquid solution or suspension, or in a solid form that is suitable for preparation as a solution or suspension in a liquid prior to injection, or as an emulsion. Additionally, transdermal administration can be accomplished by applying, pasting, rolling, attaching, pouring, pressing, rubbing, etc., of a transdermal composition onto a skin surface. These and additional methods of administration are well-known in the art. In one specific aspect, administration may include delivering a composition to a subject such that the composition circulates systemically and binds to a target cell to be taken up by endocytosis.

As used herein, the term "nucleic acid" refers to DNA and RNA, as well as synthetic congeners thereof. Non-limiting examples of nucleic acids may include plasmid DNA encoding protein or inhibitory RNA producing nucleotide sequences, synthetic sequences of single or double strands, missense, antisense, nonsense, as well as on and off and rate regulatory nucleotides that control protein, peptide, and nucleic acid production. Additionally, nucleic acids may also include, without limitation, genomic DNA, cDNA, siRNA, shRNA, mRNA, tRNA, rRNA, hybrid sequences or synthetic or semi-synthetic sequences, and of natural or artificial origin. In one aspect, a nucleotide sequence may also include those encoding for synthesis or inhibition of a therapeutic protein. Non-limiting examples of such therapeutic proteins may include anti-cancer agents, growth factors, hypoglycemic agents, anti-angiogenic agents, bacterial antigens, viral antigens, tumor antigens or metabolic enzymes. Examples of anti-cancer agents may include interleukin-2, interleukin-4, interleukin-7, interleukin-12, interleukin-15, interferon-α, interferon-β, interferon-γ, colony stimulating factor, granulocyte-macrophage stimulating factor, anti-angiogenic agents, tumor suppressor genes, thymidine kinase, eNOS, iNOS, p53, p16, TNF-α, Fas-ligand, mutated oncogenes, tumor antigens, viral antigens or bacterial antigens. In another aspect, plasmid DNA may encode for an shRNA molecule designed to inhibit protein(s) involved in the growth or maintenance of tumor cells or other hyperproliferative cells. Furthermore, in some aspects a plasmid DNA may simultaneously encode for a therapeutic protein and one or more shRNA. In other aspects a nucleic acid may also be a mixture of plasmid DNA and synthetic RNA, including sense RNA, antisense RNA, ribozymes, etc. In addition, the nucleic acid can be variable in size, ranging from oligonucleotides to chromosomes. These nucleic acids may be of human, animal, vegetable, bacterial, viral, or synthetic origin. They may be obtained by any technique known to a person skilled in the art.

As used herein, the term "concentrated" refers to a composition whose dilution has been reduced. In some aspects of the invention a "concentrated" composition comprises condensed DNA, preferably in an isotonic solution. In a particular aspect of the invention a concentrated composition comprises at least about 0.5 mg/ml of condensed DNA suspended in an isotonic solution.

As used herein, the term "polymeric backbone" is used to refer to a collection of polymeric backbone molecules having a weight average molecular weight within the designated range. As such, when a molecule such as cholesterol is described as being covalently attached thereto within a range of molar ratios, it should be understood that such a ratio represents an average number of cholesterol molecules attached to the collection of polymeric backbone molecules. For example, if cholesterol is described as being covalently attached to a polymeric backbone at a molar ratio of 0.5, then, on average, one half of the polymeric backbone molecules will have cholesterol attached. As another example, if cholesterol is described as being covalently attached to a polymeric backbone at a molar ratio of 1.0, then, on average, one cholesterol molecule will be attached to each of the polymeric backbone molecules. In reality, however, it should be understood that in this case some polymeric backbone molecules may have no cholesterol molecules attached, while other polymeric backbone molecules may have multiple cholesterol molecules attached, and that it is the average number of attached cholesterol molecules from which the ratio is derived. The same reasoning applies to the molar ratio of polyethylene glycol to the polymeric backbone.

As used herein, the term "peptide" may be used to refer to a natural or synthetic molecule comprising two or more amino acids linked by the carboxyl group of one amino acid to the alpha amino group of another. A peptide of the invention is not limited by length, and thus "peptide" can include polypeptides and proteins.

As used herein, the terms "covalent" and "covalently" refer to chemical bonds whereby electrons are shared between pairs of atoms.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The invention provides techniques whereby low concentration nucleic acid compositions (e.g., 0.15 mg/ml) may be highly concentrated without affecting the physico-chemical or biological properties of the nucleic acid or nucleic acid compositions. In one aspect, nucleic acid compositions may be concentrated by 33-fold or more without affecting these properties. These highly concentrated nucleic acid compositions allow for a wide range of dosing regimens in vivo, which have previously been tremendously challenging due to poor stability issues associated with prior attempts to achieve concentrations above ~0.3 mg/ml.

More specifically, the invention provides concentrated and stable pharmaceutical compositions, including methods for preparing and using such compositions. In one aspect, for example, a pharmaceutical composition is provided including at least about 0.5 mg/ml of a nucleic acid, where the nucleic acid is complexed with a cationic lipopolymer and the complex is suspended in an isotonic solution. The complex suspended in the isotonic comprises partially or fully condensed nucleic acid molecules. The cationic lipopolymer comprises a cationic polymer backbone having cholesterol and polyethylene glycol groups (i.e., molecules) covalently attached thereto. The molar ratio of cholesterol molecules to cationic polymer backbone is within a range of from about 0.1 to about 10, and the molar ratio of polyethylene glycol molecules to cationic polymer backbone is within a range of from about 0.1 to about 10. In another aspect, the molar ratio of polyethylene glycol molecules to cationic polymer backbone in the cationic lipopolymer is within a range of from about 1 to about 10. In yet another aspect, the molar ratio of polyethylene glycol molecules to cationic polymer backbone in the cationic lipopolymer is within a range of from about 1 to about 5. In a further aspect, the molar ratio of cholesterol molecules to cationic polymer backbone in the cationic lipopolymer is within a range of from about 0.3 to about 5. In yet a further aspect, the molar ratio of cholesterol molecules to cationic polymer backbone in the cationic lipopolymer is within a range of from about 0.4 to about 1.5.

The composition further comprises a filler excipient. The resulting composition is suitable for for delivery of the nucleic acid to a target cell to elicit, inhibit, or modify a biological response depending on the function of the nucleic acid.

In one aspect, the cholesterol and polyethylene glycol molecules may be independently and directly covalently attached to the cationic polymer backbone. In another aspect, the cholesterol and polyethylene glycol molecules are each covalently attached indirectly to the cationic polymer backbone. For example, the cholesterol molecule may be coupled, directly or indirectly via a linker or spacer, to the polyethylene glycol molecule, which is in turn covalently attached to the cationic polymer backbone. Alternatively, the cholesterol molecule may be directly attached to cationic lipopolymer backbone while the polyethylene glycol molecule is indirectly attached to the lipopolymer via a linker or spacer.

A particular linker between the polyethylene glycol and the cationic polymer backbone is an alkylene group carrying a terminal carboxy group, preferably a straight chain alkylene group of from 1 to 20 carbon atoms, and more preferably from about 2 to about 4 carbon atoms. The terminal carboxy group on the linker, when attached to an amino group of the cationic polymer backbone forms an amide bond between the cationic lipopolymer and the polyethylene glycol. A starting polyethylene glycol suitable for reacting with the cationic polymer backbone molecule is a polyethylene glycol carrying a linker molecule that is terminated by an activating group, e.g., an N-hydroxysuccinimidyl ester. One example of such a polyethylene glycol is methoxypolyethyleneglycol-propionic acid N-hydroxysuccinimidyl ester.

An example of a portion of a cationic lipopolymer structure resulting from the reaction between a polyethyleneimine, cholesteryl chloroformate (stereochemistry omitted), and methoxypolyethyleneglycol-propionic acid N-hydroxysuccinimidyl ester is the following structure. The graphic convention reflects the approximate distribution of primary, secondary and tertiary aminogroups in polyethylenimine and, for the purposes of clarity here, assumes a nonexisting regularity of polyethylenimine chain.

In various aspects of the invention, n is typically about 8 to about 20, more particularly about 10 to about 15, and even more particularly about 12; x is typically about 2 to about 3, more particularly about 2.5; y is typically about 6 to about 10, more particularly about 7 to about 9, and even more particularly 7.5; z typically is about 0.4 to about 0.8, more particularly about 0.5 to about 0.7, and even more particularly about 0.6.

Additionally, in some aspects nucleic acids that have previously been condensed using a secondary condensing system may be further condensed using the techniques presented herein to achieve greater stability of nucleic acid at high concentrations. As such, prior to condensation according to aspects of the invention, the nucleic acid may be in a partially condensed or a non-condensed form. The secondary condensing system may include any condensing material or technique known to one of ordinary skill in the art, including, but not limited to, cationic lipids, cationic peptides, cyclodextrins, cationized gelatin, dendrimers, chitosan, and combinations thereof.

Various degrees of condensation of a nucleic acid may be achieved for the composition according to aspects of the invention. In one aspect, all the nucleic acids or a substantial portion of the nucleic acids in the composition are condensed by forming complexes with the cationic polymer. In another aspect, about 30% by weight of the nucleic acids in the composition are condensed. In yet another aspect, about 50% by weight of the nucleic acid in the composition is condensed. In a further aspect, about 70% by weight of the the nucleic acid in the composition is condensed. In yet a further aspect, 90% by weight of the nucleic acid is condensed.

Additionally, the concentration of nucleic acid in the composition will vary depending on the materials used in the composition, the methods of concentration, and the intended use of the nucleic acid. In one aspect, however, the concentration of the nucleic acid is at least about 0.5 mg/ml. In another aspect, the concentration of the nucleic acid is at least about 1 mg/ml. In yet another aspect, the concentration of the nucleic acid is at least about 3 mg/ml. In a further aspect, the concentration of the nucleic acid may be at least about 5 mg/ml. In yet a further aspect, the concentration of the nucleic acid may be at least about 10 mg/ml. In another aspect, the concentration of the nucleic acid may be at least about 20 mg/ml. In yet another aspect, the concentration of the nucleic acid may be from about 10 mg/ml to about 40 mg/ml.

Various methods may be utilized to determine the degree of condensation of a nucleic acid composition. For example, in one aspect the composition may be electrophoresed to determine the degree to which nucleic acids in the composition have formed complexes with the cationic polymer

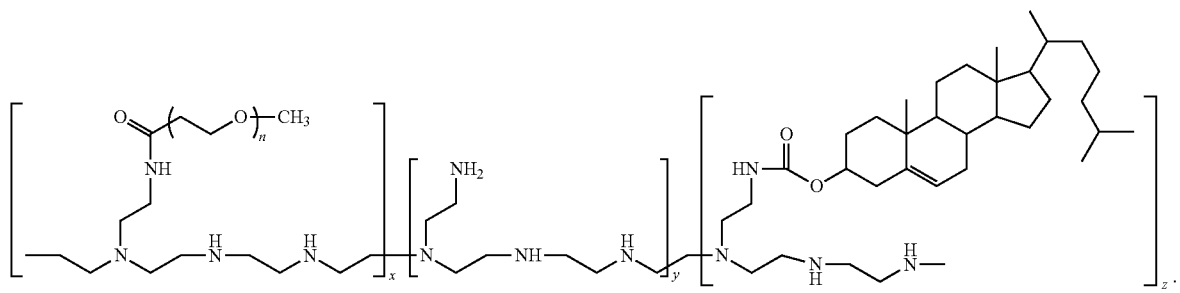

added to the composition. The electrostatic attraction of the negatively charged nucleic acid to the positively charged cationic lipopolymer inhibits the nucleic acid from moving through an agarose gel. Accordingly, following electrophoresis, nucleic acids that are condensed by complexing with the cationic polymer remain immobile in the gel, while non-condensed nucleic acids, nucleic acids not associated with the cationic polymer, will have traveled a distance relative to the strength of the electrical current in the gel. In another example, nucleic acid condensation can be determined by particle sizes within the composition. Particle size can be measured by dynamic light scattering. Typically, condensed nucleic acids will have a smaller particle size than non-condensed nucleic acids. Preferred condensed nucleic acids are those in nanoparticles of nucleic acid and cationic lipopolymer having a size of from about 50 nm to about 300 nm, more preferably from about 50-200, and even more preferably from about 50-150 nm.

Any known nucleic acid may be utilized in the compositions and methods according to aspects of the invention, including those examples described above. As such, the nucleic acids described herein should not be seen as limiting. In one aspect, for example, the nucleic acid may include a plasmid encoding for a protein, polypeptide, or peptide. Numerous peptides are well known that would prove beneficial when formulated as pharmaceutical compositions according to aspects of the invention. Non-limiting examples of a few of such peptides may include interleukin-2, interleukin-4, interleukin-7, interleukin-12, interleukin-15, interferon-α, interferon-β, interferon-γ, colony stimulating factor, granulocyte-macrophage colony stimulating factor, angiogenic agents, clotting factors, hypoglycemic agents, apoptosis factors, anti-angiogenic agents, thymidine kinase, p53, IP10, p16, TNF-α, Fas-ligand, tumor antigens, neuropeptides, viral antigens, bacterial antigens, and combinations thereof. In one specific aspect, the nucleic acid may be a plasmid encoding for interleukin-12. In another aspect, the nucleic acid may be a plasmid encoding for an inhibitory ribonucleic acid. In yet another aspect, the nucleic acid may be a synthetic short interfering ribonucleic acid. In a further aspect, the nucleic acid is an anti-sense molecule designed to inhibit expression of a therapeutic peptide.

As has been described, a cationic lipopolymer may include a cationic polymer backbone having cholesterol and polyethylene glycol covalently attached thereto. The cationic polymer backbone may include any cationic polymer known to one of ordinary skill in the art that may be used to condense and concentrate a nucleic acid according to the various aspects of the invention. In one aspect, however, the cationic polymer backbone may include polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, and combinations thereof. In one specific aspect, the cationic polymer backbone may be polyethylenimine.

In a particular aspect, the lipopolymer consists of polyethylenimine (PEI) covalently linked independently to cholesterol and polyethylene glycol. In this aspect, the average PEG:PEI:Cholesterol molar ratio in the cationic lipopolymer is about 2-3:1:0.25-1, and preferably about 2.25-2.75:1:0.4-0.8, and more preferably about 2.5:1:0.6. In a particular aspect, such a lipopolymer has a molecular weight (as the free base) of about from about 3-4 kD, preferably from about 3.25-3.75 kD, and more preferably about 3.54 kD; the corresponding hydrochloric acid salt has a molecular weight of from about 4-5 kD, preferably about 4.5 kD.

Additionally, the molecular weight of a cationic polymer backbone may vary, depending on numerous factors including the properties of the nucleic acid, the intended use of the composition, etc. In one aspect, however, the cationic polymer backbone may have a molecular weight of from about 100 to about 500,000 Daltons. Furthermore, the molecular weight of the other various components of the cationic lipopolymer may also vary. In one aspect, for example, polyethylene glycol may have a molecular weight of from about 50 to about 20,000 Daltons.

In constructing the pharmaceutical compositions of the invention, it has been discovered that the molar ratio between the amine nitrogen in the functionalized cationic lipopolymer and the phosphate in the nucleic acid (N:P ratio) may affect the degree to which the nucleic acid may be condensed and/or concentrated. Although the optimal N:P ratio may vary somewhat depending on the chemical characteristics of the nucleic acid, in one aspect the ratio of amine nitrogen in the cationic polymer backbone to phosphate in the nucleic acid is from about 0.1:1 to about 100:1. In another aspect, the ratio of amine nitrogen in the cationic polymer backbone to phosphate in the nucleic acid is from about 3:1 to about 20:1. In yet another aspect, the ratio of amine nitrogen in the cationic polymer backbone to phosphate in the nucleic acid is from about 6:1 to about 15:1. In other aspects, the ratio of amine nitrogen to phosphate in the nucleic acid is from about 3:1 to about 100:1, or about 5:1 to about 100:1, or about 7:1 to about 100:1. In a still another aspect, the ratio is from about 10:1 to about 100:1, or more preferably 10:1 to about 20:1. In one specific aspect, the ratio of amine nitrogen in the cationic polymer backbone to phosphate in the nucleic acid is about 11:1.

It is also contemplated that a filler excipient be included in the pharmaceutical composition. Such filler may provide a variety of beneficial properties to the formulation, such as cryoprotection during lyophilization and reconstitution, binding, isotonic balance, stabilization, etc. It should be understood that the filler material may vary between compositions, and the particular filler used should not be seen as limiting. In one aspect, for example, the filler excipient may include various sugars, sugar alcohols, starches, celluloses, and combinations thereof. In another aspect, the filler excipient may include lactose, sucrose, trehalose, dextrose, galactose, mannitol, maltitol, maltose, sorbitol, xylitol, mannose, glucose, fructose, polyvinyl pyrrolidone, glycine, maltodextrin, hydroxymethyl starch, gelatin, sorbitol, ficol, sodium chloride, calcium phosphate, calcium carbonate, polyethylene glycol, and combinations thereof. In yet another aspect the filler excipient may include lactose, sucrose, trehalose, dextrose, galactose, mannitol, maltitol, maltose, sorbitol, xylitol, mannose, glucose, fructose, polyvinyl pyrrolidone, glycine, maltodextrin, and combinations thereof. In one specific aspect, the filler excipient may include sucrose. In another specific aspect, the filler excipient may include lactose.

The concentration of the filler excipient in the composition may be from about 0.01% to about 5%, more particularly about 0.1% to about 3.0%, and even more particularly from about 0.1% to about 0.3%.

In some aspects it may be beneficial to functionalize the cationic lipopolymer to allow targeting of specific cells or tissues in a subject or culture. Such targeting is well known, and the examples described herein should not be seen as limiting. In one aspect, for example, the cationic lipopolymer may include a targeting moiety covalently attached to either the cationic lipopolymer or to the polyethylene glycol molecule. Such a targeting moiety may allow the cationic lipopolymer to circulate systemically in a subject to locate and specifically target a certain cell type or tissue. Examples of such targeting moieties may include transferrin, asialoglycoprotein, antibodies, antibody fragments, low density lipoproteins, cell receptors, growth factor receptors, cytokine receptors, folate, transferrin, insulin, asialoorosomucoid, mannose-6-phosphate, mannose, interleukins, GM-CSF, G-CSF, M-CSF, stem cell factors, erythropoietin, epidermal growth factor (EGF), insulin, asialoorosomucoid, mannose-6-phosphate, mannose, Lewis$^x$ and sialyl Lewis$^x$, N-acetyllactosamine, folate, galactose, lactose, and thrombomodulin, fusogenic agents such as polymixin B and hemaglutinin HA2, lysosomotrophic agents, nucleus localization signals (NLS) such as T-antigen, and combinations thereof. The selection and attachment of a particular targeting moiety is well within the knowledge of one of ordinary skill in the art.

The invention also provides lyophilized pharmaceutical compositions that may be stored for long periods of time and reconstituted prior to use. In one aspect, a lyophilized pharmaceutical composition may include a lyophilized mixture of a filler excipient and a nucleic acid condensed with a cationic lipopolymer, where the cationic lipopolymer includes a cationic polymer backbone having cholesterol and polyethylene glycol covalently attached thereto, and wherein the molar ratio of cholesterol to cationic polymer backbone is within a range of from about 0.1 to about 10, and the molar ratio of polyethylene glycol to cationic polymer backbone is within a range of from about 0.1 to about 10. The lyophilized pharmaceutical composition may be in a variety of forms, ranging from dry powders to partially reconstituted mixtures.

The invention also includes methods of making various pharmaceutical compositions containing condensed nucleic acids. In one aspect, for example, a method of making a pharmaceutical composition having a condensed nucleic acid concentrated in an isotonic solution to at least 0.5 mg/ml is provided. Such a method may include mixing a nucleic acid and a cationic lipopolymer in a filler excipient, where the cationic lipopolymer includes a cationic polymer backbone having cholesterol and polyethylene glycol covalently attached thereto, and wherein the molar ratio of cholesterol to cationic polymer backbone is within a range of from about 0.1 to about 10, and the molar ratio of polyethylene glycol to cationic polymer backbone is within a range of from about 0.1 to about 10. The mixture may be lyophilized to a powder to concentrate the nucleic acid mixture and later reconstituted with a diluent to form a solution including at least about 0.5 mg/ml condensed nucleic acid in an isotonic solution.

Generally, the composition may be obtained by mixing a nucleic acid solution with a cationic lipopolymer solution in the presence of a disaccharide sugar followed by lyophilization and reconstitution in an isotonic solution. This process is scalable, producing a few milligrams (bench scale) to several thousand milligrams (GMP scale) of the highly concentrated nucleic acid formulations with prolonged shelf life. As has been described, the cationic lipopolymer has a cationic polymer backbone to which polyethylene glycol and cholesterol are attached by covalent linkages. In the case of a polyethylenimine backbone, in one aspect the stoichiometry between polyethylene glycol and polyethylenimine and between cholesterol and polyethylenimine is in the range of 0.5-10 and 0.1-10, respectively. The chemical composition of the cationic polymer may be important to obtaining highly concentrated stable nucleic acid formulations. Cationic polymers that do not exhibit cholesterol and PEG attachment do not tend to produce stable highly concentrated formulations, as is shown in the Examples below.

The compositions according to aspects of the invention can also be combined with other condensed complexes of nucleic acid to achieve greater stability of the complexes at high nucleic acid concentrations. For example, various amounts of PEG-PEI-Cholesterol can be added to enhance the stability of other nucleic acid delivery systems that are generally unstable at high nucleic acid concentrations.

In various aspects, the synthetic delivery systems include a nucleic acid and cationic carrier which may be prepared by various techniques available in the art. A number of cationic carriers for nucleic acids are known: for example, polyethylenimine, poly(trimethylenimine), poly(tetramethylenimine), polypropylenimine, aminoglycoside-polyamine, dideoxy-diamino-b-cyclodextrin, spermine, spermidine, poly(2-dimethylamino)ethyl methacrylate, poly(lysine), poly(histidine), poly(arginine), cationized gelatin, dendrimers, chitosan, cationic lipids such as 1,2-Dioleoyl-3-Trimethylammonium-Propane (DOTAP), N-[1-(2,3-dioleoyloxy)propyl]-N,N,N-trimethylammonium chloride (DOTMA), 1-[2-(oleoyloxy)ethyl]-2-oleyl-3-(2-hydroxyethyl)imidazolinium chloride (DOTIM), 2,3-dioleyloxy-N-[2(sperminecarboxamido)ethyl]-N,N-dimethyl-1-propanaminium trifluoroacetate (DOSPA), 3β-[N—(N',N'-Dimethylaminoethane)-carbamoyl]Cholesterol Hydrochloride (DC-Cholesterol HCl) diheptadecylamidoglycyl spermidine (DOGS), N,N-distearyl-N,N-dimethyl-ammonium bromide (DDAB), N-(1,2-dimyristyloxyprop-3-yl)-N,N-dimethyl-N-hydroxyethyl ammonium bromide (DMRIE), N,N-dioleyl-N,N-dimethylammonium chloride DODAC) and combinations thereof. When these delivery systems are combined with PEG-PEI-Cholesterol, stability of the nucleic acid delivery system is increased.

Aspects of the invention also provide methods of using pharmaceutical compositions. For example, in one aspect a method of transfecting a mammalian cell may include contacting the mammalian cell with a composition as described herein, and incubating the mammalian cell under conditions to allow the composition to enter the cell and elicit biological activity of the nucleic acid. Such transfection techniques are known to those of ordinary skill in the art. Additionally, in another aspect a targeted tissue may be transfected by delivering the composition into a warm blooded organism or subject. Such delivery may be by a form of administration such as intratumoral, intraperitoneal, intravenous, intra-arterial, intratracheal, intrahepaticportal, oral, intracranial, intramuscular, intraarticular and combinations thereof. Such targeted tissue may include any tissue or subset of tissue that would benefit from transfection. For example, and without limitation, such targeted tissue may include ovary, uterus, stomach, colon, rectum, bone, blood, intestine, pancreas, breast, head, neck, lungs, spleen, liver, kidney, brain, thyroid, prostate, urinary bladder, thyroid, skin, abdominal cavity, thoracic cavity, and combinations thereof.

EXAMPLES

The following examples are provided to promote a more clear understanding of certain embodiments of the invention, and are in no way meant as a limitation thereon.

Preparation A

One gram of branched polyethyleneimine (PEI) 1800 Da (0.56 mM) is dissolved in 5 ml of chloroform and placed in a ml round bottom flask and stirred for 20 minutes at room temperature. Three hundred eighty milligrams of cholesteryl chloroformate (0.84 mM) and 500 mg of activated methoxypolyethyleneglycol (MPEG-SPA, methoxypolyethyleneglycol-propionic acid N-hydroxysuccinimidyl ester) (550 Da) (0.91 mM) are dissolved in 5 ml chloroform and transferred to an addition funnel which is located on the top of the round bottom flask containing the PEI solution. The mixture of cholesteryl chloroformate and MPEG-SPA in chloroform is slowly added to PEI solution over 5-10 minutes at room temperature. The solution is stirred for an additional 4 hrs at room temperature. After removing the solvent by a rotary evaporator, the remaining sticky material is dissolved in 20 ml of ethyl acetate with stirring. The product is precipitated from the solvent by slowly adding 20 ml of n-Hexane; the liquid is decanted from the product. The product is washed two times with a 20 ml mixture of ethyl acetate/n-Hexane (1/1; v/v). After decanting the liquid, the material is dried by purging nitrogen gas for 10-15 minutes. The material is dissolved in 10 ml of 0.05 N HCl to prepare the salt form of the amine groups. The aqueous solution is filtered through 0.2 µm filter paper. The final product is obtained by lyophilization.

The molar ratio of this example preparation is 3.0 moles of MPEG-SPA and 1.28 moles of cholesterol conjugated to one mole of PEI molecules.

Preparation B

Twenty grams (11.1 mmol) of branched PEI (BPEI) and 200 mL of dry chloroform are mixed together to dissolve the BPEI. Following dissolution, a solution containing 4 g of cholesteryl chloroformate and 18.7 g (26 mmol) of activated methoxypolyethyleneglycol (MPEG-SPA methoxypolyethyleneglycol-propionic acid N-hydroxysuccinimidyl ester, MPEG MW 550, ester MW 719) in 200 mL of dry chloroform is added dropwise to the reaction mixture with stirring over 20-30 min followed by a 3-4 hour incubation period. The mixture is then placed under vacuum to concentrate the solution and remove the residual chloroform. The resulting residue is dissolved in 320 mL of 1M aqueous HCl and stirred. This solution of PPC hydrochloride is again concentrated under vacuum, yielding a highly viscous material. To isolate PPC hydrochloride and remove the reaction byproducts and unreacted starting materials, the concentrated mixture is mixed with acetone (<0.4% water) and stirred leading to PPC hydrochloride precipitation as a free-flowing material. Following precipitation, the supernatant liquid is discarded. The hygroscopic PPC hydrochloride is dried under the vacuum.

Polymer DNA complexes are generated first by preparing PPC and DNA at the appropriate concentrations in 10% lactose. Stock solutions of cationic polymer (5 mg/ml) and DNA (3 mg/ml) in water for injection are diluted in a lactose solution ranging from 0.3-3%: these are required to achieve a final 10% lactose concentration upon reconstitution. The DNA is then added dropwise with stirring to the PPC solution and incubated for 15 min at room temperature to form the complexes.

500 µl of prepared composition is added to 2 ml borosilicate glass vials and placed in a freedryer. Vials are cooled to −34° C. for 4 hours before the start of the primary drying. After 24 hours, the shelf temperature is raised to 20° C. and kept under vacuum for another 24 hours. Finally the shelf temperature is raised to 4° C. and vials are capped under vacuum.

Preparation C

One hundred eighty milligrams of branched PEI 1800 (0.1 mM) is dissolved in 4 ml of chloroformate and stirred for 30 minutes at room temperature. Seventy milligrams of cholesteryl chloroformate (0.14 mM) and 48 mg PEG 330 (0.14 mM) are dissolved in 1 ml of chloroformate, and slowly added to the PEI solution over 3-10 minutes using a syringe. The mixture is stirred for 4 hrs at room temperature. After addition of 10 ml of ethyl acetate for precipitation, the solution is incubated overnight at −20° C., and then the liquid is decanted from the flask. The remaining material is washed 2 times with a 5 ml mixture of ethyl acetate/n-Hexane (1/1; v/v). The remaining material is dried by nitrogen purge for 10-15 minutes, dissolved in 10 ml of 0.05N HCl for 20 minutes, and then the solution is filtered through a 0.2 µm syringe filter. The aqueous solution is lyophilized by freeze drying to remove water from the polymers.

The molar ratio of this preparation is 0.85 moles of PEG and 0.9 moles of cholesterol conjugated to one mole of PEI molecules.

Preparation D

Five hundred milligrams of 25 kDa linear PEI (0.02 mM) is dissolved in 30 ml and stirred at 65° C. for 30 minutes. The three-neck flask is equipped with a condensation and addition funnel. A mixture of 200 mg of mPEG-NHS 1000 (0.2 mM) and 40 mg cholesteryl chloroformate (0.08 mM) in 5 ml chloroform is slowly added to the PEI solution over 3-10 minutes. The solution is stirred constantly for an additional 4 hrs at 65° C., and then volume is reduced to about 5 ml in a rotary evaporator. The solution is precipitated in 50 ml of ethyl ether to remove free cholesterol, the liquid is decanted from the flask, and the remaining material is washed two times with 20 ml of ethyl ether. After drying with pure nitrogen, the material is dissolved in a mixture of 10 ml of 2.0 N HCl and 2 ml of trifluoroacetic acid. The solution is dialyzed against deionized water using a MWCO 15000 dialysis tube for 48 hrs with changing of fresh water every 12 hrs. The solution is lyophilized to remove water.

The molar ratio of this preparation is 12.0 moles of PEG and 5.0 moles of cholesterol conjugated to one mole of PEI molecules.

Preparation E

One gram of PEI (MW: 1200 Daltons) is dissolved in a mixture of 15 mL of anhydrous methylene chloride and 100 µl of triethylamine (TEA). After stirring on ice for 30 minutes, 1.2 g of cholesteryl chloroformate solution is slowly added to the PEI solution and the mixture is stirred overnight on ice. The resulting product is precipitated by adding ethyl ether followed by centrifugation and subsequent washing with additional ethyl ether and acetone. Water-insoluble lipopolymer is dissolved in chloroform to give a final concentration of 0.08 g/mL. Following synthesis and purification, the water-insoluble lipopolymer is characterized using MALDI-TOFF MS and $^1$H NMR.

The NMR measurement of water insoluble lipopolymer 1200 shows the amount of cholesterol conjugated to the PEI is about 40%. MALDI-TOF mass spectrometric analysis of the water-insoluble lipopolymer shows its molecular weight to be approximately 1600.

Preparation F

Three grams of PEI (MW: 1800 Daltons) is stirred for 30 minutes on ice in a mixture of 10 ml of anhydrous ethylene chloride and 100 µl of triethylamine. One gram of cholesteryl chloroformate is dissolved in 5 ml of anhydrous ice-cold methylene chloride and then slowly added over 30 minutes to the PEI solution. The mixture is stirred for 12 hours on ice and the resulting product is dried in a rotary evaporator. The powder is dissolved in 50 ml of 0.1 N HCl. The aqueous solution is extracted three times with 100 mL of methylene chloride, and then filtered through a glass microfiber filter. The product is concentrated by solvent evaporation, precipitated with a large excess of acetone, and dried under vacuum. The product is analyzed using MALDI-TOF mass spectrophotometry and 10 $^1$H NMR. The NMR results of water soluble lipopolymer 1800 show the amount of cholesterol conjugated to PEI is about 47%. MALDI-TOFF mass spectrometric analysis of PEACE shows its molecular weight to be approximately 2200. This suggests that the majority of PEACE 1800 is of a 1/1 molar ratio of cholesterol and PEI, although some were either not conjugated or are conjugated at a molar ratio of 2/1 (cholesterol/PEI).

Preparation G

Fifty milligrams PEI 1800 is dissolved in 2 mL of anhydrous methylene chloride on ice. Then, 200 µL of benzyl chloroformate is slowly added to the reaction mixture and the solution is stirred for four hours on ice. Following stirring, 10 mL of methylene chloride is added and the solution is extracted with 15 mL of saturated NH$_4$Cl. Water is removed from the methylene chloride phase using magnesium sulfate. The solution volume is reduced under vacuum and the product, CBZ protected PEI is precipitated with ethyl ether. Fifty milligrams of primary amine CBZ protected PEI is dissolved in methylene chloride, 10 mg of cholesterol chloroformate is added, and the solution is stirred for 12 hours on ice. The product CBZ protected lipopolymer, is precipitated with ethyl ether, washed with acetone, and then dissolved in DMF containing palladium activated carbon as a catalyst under H$_2$ as a hydrogen donor. The mixture is stirred for 15 hours at room temperature, filtered through CELITE®, and the solution volume is reduced by a rotary evaporator. The final product is obtained from precipitation with ethyl ether.

Preparation H

Five hundred milligrams of NH$_2$—PEG-COOH 3400 (0.15 mM) was dissolved in 5 ml of anhydrous chloroform at room temperature for 30 minutes. A solution of 676 mg of cholesterol chloroformate (1.5 mM) in 1 ml of anhydrous chloroform is slowly added to the PEG solution and then stirred for an additional 4 hrs at room temperature. The mixture is precipitated in 500 ml of ethyl ether on ice for 1 hr, and then washed three times with ethyl ether to remove the non-conjugated cholesterol. After drying with nitrogen purge, the powder is dissolved in 5 ml of 0.05N HCl for acidifying the carboxyl groups on the PEG. The material is dried by freeze drier. One hundred milligrams of PEI 1800 (0.056 mM), 50 mg of DCC, and 50 mg of NHS are dissolved in 5 ml of chloroform at room temperature, the mixture is stirred for 20 min, and then a solution of 380 mg of chol-PEG-COOH in 1 ml of chloroform is slowly added to the PEI solution. After stirring for six hours at room temperature, the organic solvent was removed with a rotary evaporator. The remaining material was dissolved in 10 ml of deionized water and purified by FPLC.

Example 1

Preparation of Concentrated Liquid Formulations of Condensed Nucleic Acid with a Cationic Lipopolymer This example illustrates preparation of highly concentrated formulations of fully condensed nucleic acid at bench-scale production. This involves preparation of nucleic acid complexes with a cationic polymer followed by lyophilization and reconstitution to isotonic solutions. The nucleic acid used is a plasmid DNA encoding for IL-12 or luciferase gene, and the polymer comprised a polyethylenimine (PEI) backbone covalently linked to polyethylene glycol (PEG) and cholesterol (Chol) (PEG-PEI-Chol or PPC). The molar ratio between PEG and PEI and between cholesterol and PEI is 0.5-10 and 0.1-10, respectively. First, the DNA and PPC solutions are separately prepared at 5 mg/ml in water for injection and subsequently diluted to 0.15 mg/ml (DNA) and 0.554 mg/ml (PPC) at 3% lactose. The DNA in lactose solution is added to the PPC in lactose solution using a micropipette to a nitrogen to phosphate ratio (N:P ratio) of 11:1, and the formulation is incubated for 15 minutes at room temperature to allow the complexes to form. The PPC/DNA complexes in 3% lactose are lyophilized using a FREEZONE freeze dry System from LABCONCO Corp. Kansas City, Mo. 500 µl of prepared formulation is added to 2 ml borosilicate glass vials which were then lyophilized using a freeze drying program consisting of the following segments:

1) freezing segment (Ramp 0.25° C./min, hold at 34° C. for 4 hrs),
2) primary drying segment (hold at 34° C. for 24 hrs),
3) secondary drying segment (Ramp to 20° C. and hold for 24 hrs), and
4) Ramp to 4° C. at 0.25° C./min.

The resultant lyophilized powder is reconstituted with water for injection to various concentrations ranging from 0.1 mg/ml to 20 mg/ml DNA. A typical batch of small-scale preparation amounted to 100-200 mg of fully formulated DNA.

Example 1A

A nucleic acid/cationic lipopolymer formulation is prepared essentially according to the procedure outlined above in Example 1 using a cationic lipopolymer and IL-12 nucleic acid at an N:P ratio of 11:1. The cationic lipopolymer has a PEG:PEI:Cholesterol molar ratio of about 2.5:1:0.6, and a molecular weight (as the free base) of about 3.54 kD. The resulting formulation containing lactose is lyophilized and can be reconstituted to nucleic acid concentrations of at least about 0.5 mg/ml without agglomeration of the nucleic acid or loss of significant transfection activity.

Example 2

Preparation of Concentrated Liquid Formulations of Condensed Nucleic Acid with a Cationic Lipopolymer This example illustrates a preparation of highly concentrated formulations of condensed nucleic acid, as is shown in FIG. 1. This protocol has produced over 6000 mg of fully formulated DNA (as compared to 100-200 mg DNA produced from the small-scale preparation described in Example 1) and can be expanded to even higher production amounts. The scaled-up method involved mixing of the bulk DNA and polymer solutions with a peristaltic pump achieving an online mixing scenario to form the complexes followed by freeze-drying cycles compatible for large load. Briefly, the DNA and PPC solutions are prepared at 0.3 mg/ml and 1.1 mg/ml in 3% lactose, respectively. The two components are combined at a constant flow rate using a peristaltic pump (WATSON MARLOW, SCI 400) with a 0.89 mm internal diameter of silicon tubing (WATSON MARLOW, Z982-0088) at a flow rate of 225±25 ml/min. The two mixtures are joined by a polypropylene T-connector at the end of each tube. Mixing polymer and DNA solutions resulted in instant formation of nanoparticles. Forty milliliters of the formulated complexes are placed in 100 ml glass vials and lyophilized using a freeze-drying program consisting of the following segments:

1) pre-freeze at −50 C for up to 720 minutes,
2) primary drying at −40 C for up to 180 minutes and then at −34 C for up to 1980 minutes at 65 µm Hg, and
3) secondary drying at −25 C for up to 720 minutes, −15 C for up to 3180 minutes, −10 C for up to 1500 minutes, and 4 C for up to 1440 minutes at 65 µm Hg.

The resultant lyophilized powder is reconstituted with water for injection to various concentrations ranging from 0.1 mg/ml to 20 mg/ml DNA. A typical batch of this scale amounts to 6000 mg of fully formulated DNA.

Example 3

Measurement of the Particle Size of Concentrated Liquid Formulations of Condensed Nucleic Acid with a Cationic Lipopolymer Highly concentrated formulations of plasmid DNA with cationic lipopolymer, PPC, are prepared as described in Examples 1 and 2. For polymer/nucleic acid particle size measurement, an aliquot of the liquid formulation is analyzed using 90Plus/BI-MAS Particle Sizer from BROOKHAVEN INSTRUMENTS Corp., Holtsville, N.Y. Specifically, 50 µl of formulation is added to 950 µl of milli-Q water in polystyrene cuvets for analysis.

FIG. 2A and FIG. 2B illustrate the particle size of DNA/PPC complexes in pre-lyophilized or non-concentrated formulations (0.15 mg/ml DNA) and after reconstitution at higher concentrations ranging from 0.5 mg/ml to 10 mg/ml with IL-12 plasmid (FIG. 2A) or luciferase plasmid (FIG. 2B). Reconstitution at higher concentrations does not significantly influence the particle size, which suggests that the complexes are stable.

Example 4

Analysis of the Nucleic Acid Condensation of Concentrated Liquid Formulations of Nucleic Acid with a Cationic Lipopolymer The ability of PPC polymer to condense plasmid DNA is evaluated in this example. Highly concentrated formulations of plasmid DNA with cationic lipopolymer, PPC, are prepared as described in Examples 1 and 2. The nucleic acid/polymer complexes are electrophoresed using 1% agarose gel. The electrostatic attraction of negatively charged plasmid DNA to the positively charged PPC polymer prevents the DNA from traveling through the agarose gel. As shown in FIG. 3, all of the DNA present in the highly concentrated formulations is condensed.

Example 5

Measurement of Nucleic Acid Concentration in Concentrated Liquid Formulation of Nucleic Acid with a Cationic Lipopolymer The amount of nucleic acid in highly concentrated formulations of DNA and PPC complexes are quantified using an AGILENT 8453 spectrophotometer (AGILENT TECHNOLOGIES, Inc. Santa Clara, Calif.). 50 µl of formulation is diluted with 950 µl water for injection (WFI) in a quartz cuvette and absorbance is measured using 260 nm wavelength. DNA concentration is determined assuming 1 Optical density (at 260 nm)=50 µg/ml of DNA.

Example 6

Measurement of Transfection Activity of Concentrated Liquid Formulations of Nucleic Acid with a Cationic Lipopolymer The transfection activity of highly concentrated formulations of DNA and PPC complexes is determined in vitro. Direct comparison is made to that of a non-concentrated formulation. Transfection complexes containing luciferase or IL-12 plasmid are prepared by methods described in Examples 1 and 2, and reconstituted at DNA concentrations ranging from 0.15 mg/ml to 10 mg/ml. Cos-1 cells ($1.5 \times 10^5$ cell/well) are seeded into 12-well tissue culture plates in 10% fetal bovine serum (FBS). Each well is incubated for 6 hours with 4 µg of complexed DNA in absence of FBS in a total volume of 500 µl of Dulbecco/Vogt Modified Eagle's Minimal Essential Medium (DMEM). When the incubation period is concluded, medium is replaced with 1 ml fresh DMEM supplemented with 10% FBS for another 40 hours. At the end of the incubation period, transfection activity was measured in the cell culture medium (IL-12) or cell lysate (luciferase). For measurement of IL-12 levels, cell culture medium is directly analyzed by an IL-12 ELISA assay. For luciferase measurement, cells are washed with phosphate-buffered saline and lysed with TENT buffer (50 mM Tris-Cl [pH8.0] 2 Mm EDTA, 150 mM NaCl, 1% Triton X-100). Luciferase activity in the cell lysate is measured as relative light units (RLU) using an Orion Microplate Luminometer (BERTHOLD DETECTION SYSTEMS, Oak Ridge, Tenn.). The final values of luciferase are reported in terms of RLU/mg total protein. The total protein level is determined using a BCA protein assay kit (PIERCE BIOTECHNOLOGY, Inc., Rockford, Ill.). The levels of IL-12 and luciferase expression from highly concentrated formulations of IL-12 and luciferase plasmid/PPC complexes are shown in FIG. 4A and FIG. 4B, respectively. The data shows transfection activity of nucleic acid complexes in highly concentrated form is preserved.

Example 7

Evaluating Various Excipient Sugars in the Preparation of Concentrated Liquid Formulations of Nucleic Acid with Cationic Lipopolymer and Characterization Thereof Two commonly used sugars, lactose and sucrose, are evaluated as potential bulking or filler agents during lyophilization process for the preparation of highly concentrated formulations. PPC/DNA complex are prepared in lactose and sucrose each at 3%, 1.5% and 0.3%. Formulations are lyophilized using protocol as in Example 1. Following the freeze-drying process, formulations are reconstituted with WFI to a final DNA concentration of 0.5 mg/ml, 1 mg/ml and 5 mg/ml. Particle size and in vitro gene transfer are evaluated for these various formulation. As shown in Table 1, both particle size and transfection activity is preserved whether the cryoprotectant filler is sucrose or lactose. These results show more than one type of sugar can be used to prepare physico-chemically and biologically stable high concentrations of nucleic acid with cationic polymer.

TABLE 1

Evaluation of excipient sugars in the preparation of concentrated isotonic formulations of nucleic acid with cationic polymer.

| Lactose (w/v) | | DNA (mg/m) | | Particle size (nm) | | Luc Expression (RLU/mg protein) | |
|---|---|---|---|---|---|---|---|
| Pre-Lyo. | Post-Lyo. | Pre-Lyo. | Post-Lyo. | Pre-Lyo. | Post-Lyo. | Pre-Lyo. | Post-Lyo. |
| 10.0% | N/A | 0.15 | N/A | 117.00 | N/A | 8,160.748 | |
| 3.0% | 10.0% | 0.15 | 0.50 | 123.00 | 200.00 | | 9,484,771.98 |
| 1.5% | 10.0% | 0.15 | 1.0 | 121.00 | 135.00 | | 7,492,002.47 |
| 0.3% | 10.0% | 0.15 | 5.00 | 150.00 | 209.00 | | 6,442,482.87 |

| Sucrose (w/v) | | DNA (mg/m) | | Particle size (nm) | | Luc Expression (RLU/mg protein) | |
|---|---|---|---|---|---|---|---|
| Pre-Lyo. | Post-Lyo. | Pre-Lyo. | Post-Lyo. | Pre-Lyo. | Post-Lyo. | Pre-Lyo. | Post-Lyo. |
| 10.0% | N/A | 0.15 | N/A | 160.00 | N/A | 12,698,431 | |
| 3.0% | 10.0% | 0.15 | 0.50 | 137.00 | 154.00 | | 5,995,053 |
| 1.5% | 10.0% | 0.15 | 1.00 | 125.00 | 206.00 | | 8,004,970 |
| 0.3% | 10.0% | 0.15 | 5.00 | 131.00 | 244.00 | | 9,066,137 |

Example 8

IL-12 Expression in Normal Brain Parenchyma after Intracranial Expression of Concentrated Liquid Formulations of Nucleic Acid with Cationic Lipopolymer Direct administration of IL-12 plasmid with cationic polymer, PPC, in normal brain tissue is examined to determine if highly concentrated formulation of nucleic acid and cationic lipopolymer is biologically active in vivo. Immunohistochemcial staining for IL-12 is performed on slices of brains from animals euthanized 14 days or 1 month after treatment. Brain parenchyma of animals treated with PPC alone did not show any IL-12 staining (FIG. 5A). In contrast, brain parenchyma of mice injected with pmIL-12/PPC intracranially stained positive for IL-12 (FIG. 5B). This experiment demonstrates biological activity of nucleic acid complexes with a cationic polymer is preserved during the concentration process. In addition, it can be concluded that the cytokine remains present for at least a month after injection. Moreover, the presence of this cytokine in the brains of animals that remained alive until euthanized suggests that the actual expression of IL-12 does not cause lethal toxicity in brain.

Example 9

Figure 6:
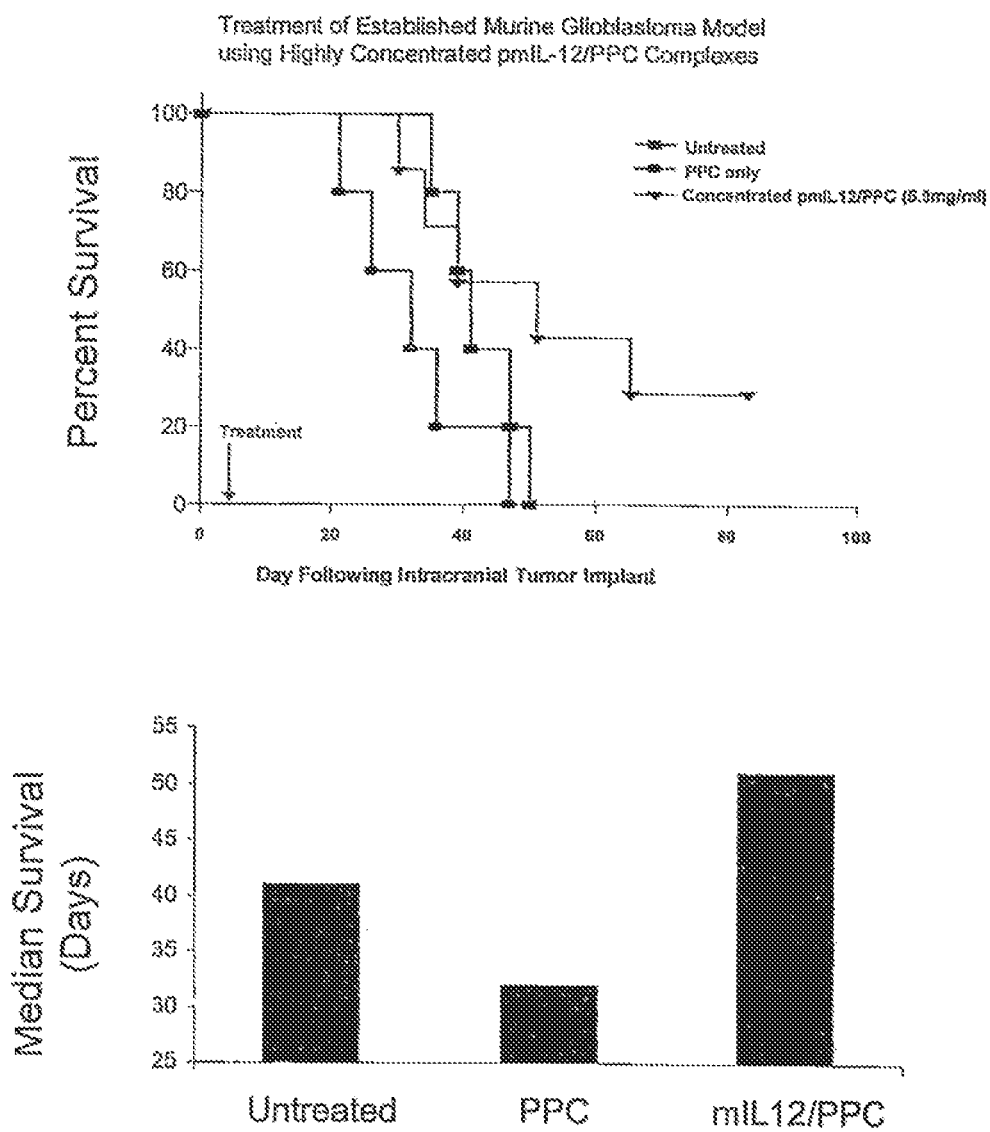
FIG. 6 shows two graphs of anticancer efficacy of IL-12 with lipopolymer compared with controls.
Figure 7A:
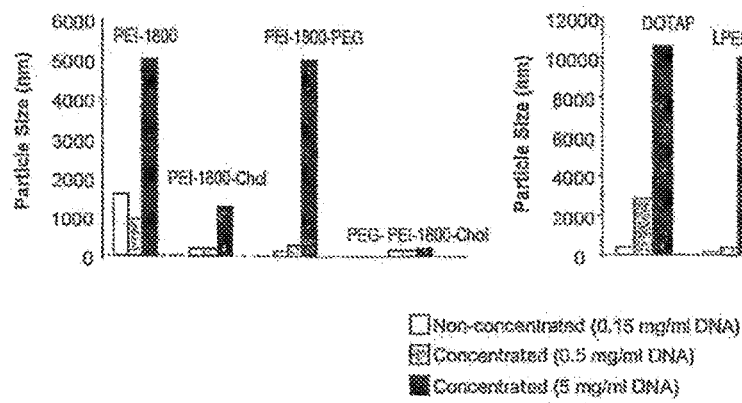
FIG. 7A and FIG. 7B are graphs of particle size of various nucleic acid/cationic polymer mixtures.
Figure 7B:
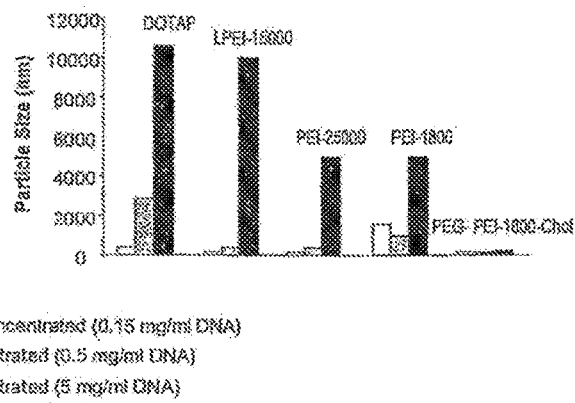
Figure 8A:
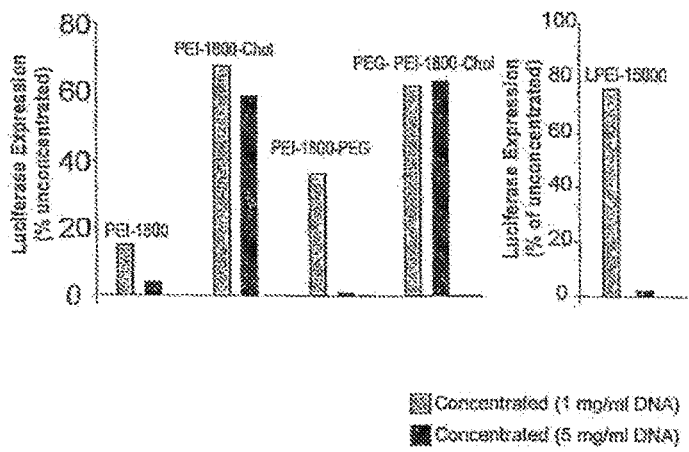
FIG. 8A and FIG. 8B are graphs of luciferase expression of resulting from various nucleic acid/cationic polymer mixtures.
Figure 8B:
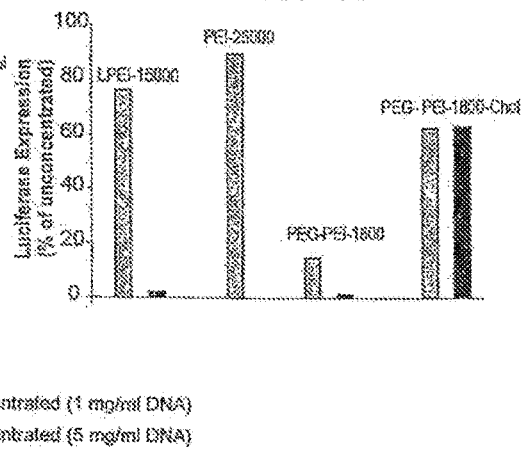

Efficacy of Concentrated Liquid Formulations of Nucleic Acid with Cationic Lipopolymer in a Mouse Glioma Model The anticancer efficacy of highly concentrated formulations of fully complexed nucleic acid expressing 1-12 gene is examined in a mouse glioma model. Tumors are implanted in the cerebral cortex of mice by intracranial injection of $1\times10^5$ GL261 glioma cells together with the co-injection of 3 µl of IL-12/PPC complexes from highly concentrated formulation of 5 mg/ml IL-12 plasmid DNA. The animals are monitored for any sign of neurotoxicity and autopsied, when possible, to confirm that death is due to the intracranial tumour. Survival is plotted using a Kaplan-Meier survival analysis. A single intracranial injection of pmIL-12/PPC complexes administered at 15 µg plasmid dose is well tolerated as no significant adverse effects are observed. A single injection of pmIL-12/PPC complexes at 15 µg plasmid dose produced a significant enhancement in animal survival (FIG. 6).

Example 10

Biological Activity of Concentrated Liquid Formulations of Nucleic Acid with Cationic Lipopolymer in Ovarian Cancer Patients The biological activity of highly concentrated formulation of fully condensed nucleic acid expressing IL-12 gene is examined in a patients with recurrent ovarian cancer. Four weekly intraperitoneal administrations of highly concentrated isotonic formulations of IL-12 plasmid and PPC in women with recurrent ovarian cancer produced significant levels of IFN-γ, a surrogate marker of IL-12, in peritoneal fluid of treated patients. The IFN-γ levels vary from 20 to 275 pg/ml peritoneal fluid. These data demonstrates that the highly concentrated formulation of IL-12 nucleic acid is suitable for clinical application.

Example 11

Evaluating the Effect of Chemical Composition of Cationic Polymer on the Properties of Concentrated Liquid Formulations of Nucleic Acid with Cationic Lipopolymer Previous attempts have demonstrated that concentrating nucleic acid formulations with cationic gene carriers such as lipid or polymers is highly challenging due to poor stability and loss of transfection as a result of the concentration process. To determine if the success in producing physico-chemically and biologically stable high concentrations of fully condensed nucleic acid is unique to the chemical composition of the test cationic polymer, PEG-PEI-Cholesterol (PPC), other cationic polymers are tested, including that of free PEI, PEI linked to cholesterol or PEI linked to PEG and a cationic liposome DOTAP. DNA complexes are prepared at 0.15 mg/ml and then concentrated to 0.5 and 5 mg/ml as described in Example 1. Particle size and transfection activity is determined as described in Example 3 & 6. As shown in FIGS. 7A, 7B, 8A, and 8B, DNA complexes prepared with free PEI (PEI1800, PEI15000, PEI 25000) or PEI-Cholesterol, PEI-PEG or cationic lipid DOTAP did not produce stable complexes as these complexes aggregated and lost transfection activity after lyophilization and reconstitution to 0.5 mg/ml or 5 mg/ml. The destabilizing effects are more prominent at 5 mg/ml than at 0.5 mg/ml. In comparison, DNA complexes prepared with PEG-PEI-cholesterol (PPC) maintain their physico-chemical and transfection properties during lyophilization and reconstitution at high DNA concentrations (FIGS. 7A, 7B, 8A, and 8B). These results suggest covalent modification of cationic polymer with cholesterol and PEG is critical to activity preservation during the concentration process.

Example 12

Figure 9:
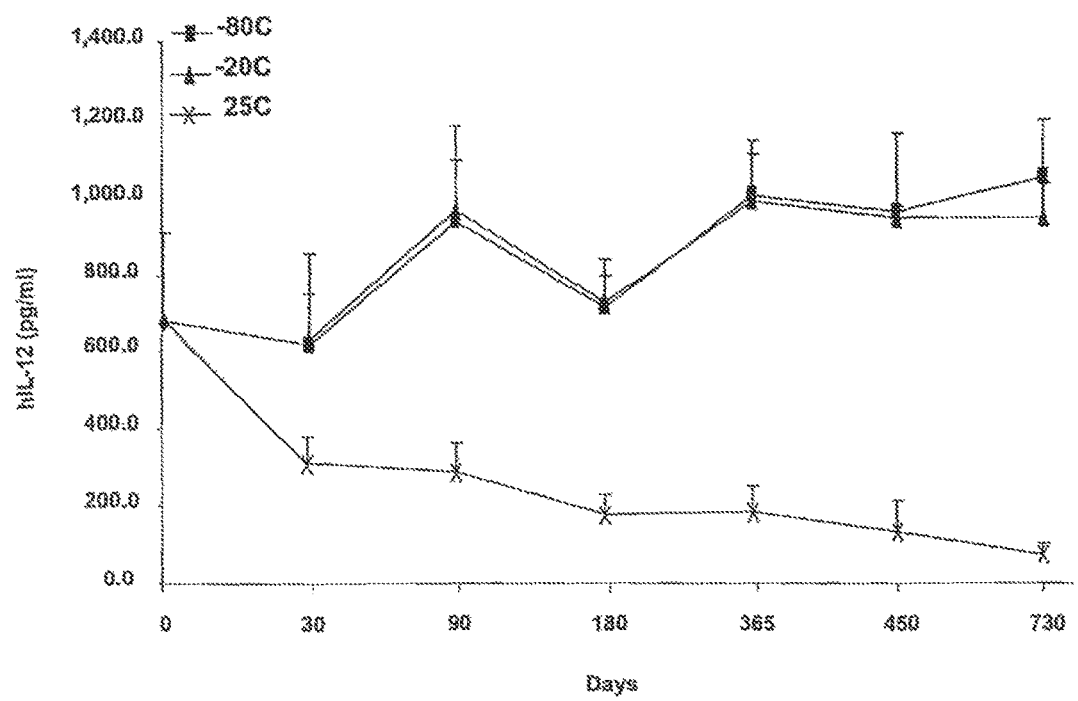
FIG. 9 is a graph showing the biological activity of a nucleic acid/cationic lipopolymer composition after long-term storage.

Long-Term Stability of the Lyophilized or Concentrated Liquid Formulations of Nucleic Acid with Cationic Polymer Large scale lots of lyophilized IL-12/PPC complexes are prepared under cGMP with the method outlined in Example 2 and stored at −80° C., −20° C., 4° C., and 25° C. (60% RH) for stability evaluation. At the time of analysis, vials are removed from storage and 2.4 mL of WFI is added. For each sample pH, DNA concentration, osmolality, particle size and biological activity measured. As shown in FIG. 9, the DNA concentration, pH, osmolality and particle size of the IL-12/PPC complexes are maintained during the two-year storage at the indicated temperatures. The gene transfer activity of pIL-12/PPC is quantified in COS-1 cells as described in Example 6. The COS-1 cells are transfected with the biological material at 4 µg DNA. The levels of IL-12 in cell culture media are quantified 48 hours after the transfection with a commercially available ELISA kit. The bioactivity results from the two-year stability study are illustrated in FIG. 9. There is no significant change in bioactivity of the biological product during the storage period at −80° C. or −20° C. At time 0, the activity is 151±130 pg/mL and the rest of the data fluctuates within this standard deviation, except for 25° C. where there is a consistent decline over time. At 4 C a drop in transfection activity is observed at 360 days but due to insufficient samples no follow up time points are available to reach a conclusive assessment.

Example 13

Stability of the Reconstituted Material of Concentrated Liquid Formulations of Nucleic Acid with Cationic Polymer The stability of reconstituted material is examined in a separate study. Lyophilized IL-12 plasmid DNA/PPC complexes are prepared according to the method described in Example 2, and reconstituted in water for injection to 0.5 mg/ml. The reconstituted material is stored at 4° C. Samples are removed on day 60 and 90 and analyzed for particle size, osmolality, and gene expression. The lyophilized product stored in sealed vials at −80° C. is analyzed simultaneously for comparison. As shown in Table 2, the reconstituted EGEN-001 is stable at 4° C. for at least 90 days after reconstitution with WFI. None of the stability parameters including DNA concentration, particle size, osmolality or gene expression is significantly altered when compared to the lyophilized material stored in sealed vials at −80° C.

TABLE 2

Long-term stability of the reconstituted form of highly concentrated and fully condensed isotonic formulations of nucleic acid with cationic polymer at 4 C.

| Stability Parameters | Days | | | | | |
|---|---|---|---|---|---|---|
| | 0 | 60 | 90 | 180 | 270 | 365 |
| Particle size (nm) | 102 | 98 | 101 | 97 | 103 | 98 |
| Osmolarity (mOsmole) | 303 | 309 | 303 | 312 | 312 | 306 |
| pH | 2.75 | 2.66 | 2.69 | 2.7 | 2.73 | 2.59 |
| DNA (mg/ml) | 0.49 | 0.49 | 0.50 | 0.47 | 0.50 | 0.50 |
| IL-12 Expression (pg/ml) | 1220 | 1681 | 1164 | 1062 | 1409 | 476.3 |

Example 14

Preparation of Highly Concentrated Stable DNA Formulations of Synthetic Nucleic Acid Delivery Systems by Co-Formulating with PEG-PEI-Cholesterol PEG-PEI-Cholesterol is added to existing, synthetic nucleic acid delivery systems to enhance the stability of nucleic acid formulations that are generally unstable at high nucleic acid concentrations.

In one example, PEG-PEI-Cholesterol is added to DNA formulations prepared with linear polyethylenimine 25 kDa (LPEI25 kD). DNA formulations at 0.15 mg/ml concentration can be prepared with LPEI25 kD at 10:1 (N:P ratio) in presence of 3% lactose. PEG-PEI-Cholesterol lipopolymer may then be added to LPEI25 kD/DNA complex at various PPC ratios to formulated DNA. For example, PPC/DNA (N:P ratios) can be (0:1), (1:1), (5:1), (7.5:1), (11:1), (15:1), and (20:1). 500 µl of each formulation can be added to 2 ml of borosilicate glass vials and then lyophilized in a freeze dry system. The freeze drying program consists of the following segments:

1) Freezing segment (Ramp 0.25° C./min, hold at −34° C. for 4 hrs),
2) Primary drying segment (hold at −34° C. for 24 hrs),
3) Secondary drying segment (Ramp to −20° C. and hold for 24 hrs), and
4) Ramp to 4° C. at 0.25° C./min.

The lyophilized formulations may be reconstituted with water for injection to 0.5 mg/ml or other suitable concentration.

It is to be understood that the above-described compositions and modes of application are only illustrative of preferred embodiments of the invention. Numerous modifications and alternative arrangements may be devised by those skilled in the art without departing from the spirit and scope of the invention and the appended claims are intended to cover such modifications and arrangements. Thus, while the invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of transfecting a mammalian cell, comprising: contacting the mammalian cell with a reconstituted composition comprising a nucleic acid, a cationic lipopolymer, and a filler excipient in an aqueous medium, wherein the cationic lipopolymer consists of polyethyleneimine (PEI) covalently linked independently to cholesterol and/or polyethylene glycol (PEG) groups, wherein the average PEG:PEI:cholesterol molar ratio in the cationic lipopolymer is within the range of 1-5 PEG:1 PEI:0.4-1.5 cholesterol, wherein the nucleic acid and cationic lipopolymer form a complex; and wherein the complex of the reconstituted composition enters the mammalian cell and elicits biological activity of the nucleic acid.

2. The method of claim 1, wherein the mammalian cell is an ovarian cancer cell.

3. The method of claim 1, wherein the mammalian cell is a glioma cell.

4. The method of claim 1, wherein the nucleic acid comprises a polynucleotide encoding a protein selected from the group consisting of interleukin-2, interleukin-4, interleukin-7, interleukin-12, interleukin-15, interferon-α, interferon-β, interferon-γ, colony stimulating factor, granulocyte-macrophage colony stimulating factor, angiogenic agents, clotting factors, hypoglycemic agents, apoptosis factors, anti-angiogenic agents, thymidine kinase, p53, IP10, p16, TNF-α, Fas-ligand, tumor antigens, neuropeptides, viral antigens, bacterial antigens, and combinations thereof.

5. The method of claim 1, wherein the nucleic acid is a plasmid comprising a polynucleotide encoding interleukin-12.

6. The method of claim 1, wherein the nucleic acid comprises an inhibitory ribonucleic acid or a synthetic short interfering ribonucleic acid.

7. The method of claim 1, wherein the filler excipient is selected from the group consisting of a sugar, a sugar alcohol, a starch, a cellulose, and combinations thereof.

8. The method of claim 1, wherein the filler excipient is selected from the group consisting of lactose, sucrose, trehalose, dextrose, galactose, mannitol, maltitol, maltose, sorbitol, xylitol, mannose, glucose, fructose, polyvinyl pyrrolidone, glycine, maltodextrin, hydroxymethyl starch, gelatin, sorbitol, ficol, sodium chloride, calcium phosphate, calcium carbonate, polyethylene glycol, and combinations thereof.

9. The method of claim 1, wherein the ratio of amine nitrogen in the cationic lipopolymer to phosphate in the nucleic acid is from about 0.1:1 to about 100:1.

10. The method of claim 1, wherein the cationic polymer has a molecular weight of from about 50 to about 500,000 Daltons.

11. The method of claim 1, wherein the particle size of the complex remains constant at 4° C. for at least 90 days following reconstitution.

12. The method of claim 1, wherein the reconstituted composition has a nucleic acid concentration of at least 0.5 mg/ml without agglomeration of the nucleic acid.

13. A method of transfecting a targeted tissue of a subject, comprising administering to the subject a reconstituted composition comprising a nucleic acid, a cationic lipopolymer, and a filler excipient in an aqueous medium, wherein the cationic lipopolymer consists of polyethyleneimine (PEI) covalently linked independently to cholesterol and/or polyethylene glycol (PEG) groups, wherein the average PEG:PEI:cholesterol molar ratio in the cationic lipopolymer is within the range of 1-5 PEG:1 PEI:0.4-1.5 cholesterol, and wherein the nucleic acid and cationic lipopolymer form a complex, wherein the complex of the reconstituted composition enters the targeted tissue and elicits biological activity of the nucleic acid.

14. The method of claim 13, wherein the administration is selected from the group consisting of intratumoral, intraperitoneal, intravenous, intraarterial, intratracheal, intrahepaticportal, oral, intracranial, intramuscular, intraarticular and combinations thereof.

15. The method of claim 13, wherein the targeted tissue is selected from the group consisting of ovary, uterus, stomach, colon, rectum, bone, blood, intestine, pancreas, breast, head, neck, lungs, spleen, liver, kidney, brain, thyroid, prostate, urinary bladder, thyroid, skin, abdominal cavity, thoracic cavity, and combinations thereof.

16. The method of claim 13, wherein the subject is a human; the administration is intraperitoneal; the target tissue is the ovary or abdominal cavity; and the nucleic acid comprises a polynucleotide encoding interleukin-12.

17. The method of claim 13, wherein the subject is a human; the administration is intracranial; the target tissue is brain; and the nucleic acid comprises a polynucleotide encoding interleukin-12.

18. A method for treating a cancer in a subject comprising administering to a subject in need thereof a reconstituted composition comprising a nucleic acid, a cationic lipopolymer, and a filler excipient in an aqueous medium, wherein the cationic lipopolymer consists of polyethyleneimine (PEI) covalently linked independently to cholesterol and/or polyethylene glycol (PEG) groups, wherein the average PEG:PEI:cholesterol molar ratio in the cationic lipopolymer is within the range of 1-5 PEG:1 PEI:0.4-1.5 cholesterol, and wherein the nucleic acid and cationic lipopolymer form a complex, wherein the complex of the reconstituted composition enters cancer cells of the subject and elicits biological activity of the nucleic acid.

19. The method of claim 18, wherein the administration is selected from the group consisting of intratumoral, intraperitoneal, intravenous, intra-arterial, intratracheal, intrahepaticportal, oral, intracranial, intramuscular, intraarticular and combinations thereof.

20. The method of claim 18, wherein the cancer is in a target tissue selected from the group consisting of ovary, uterus, stomach, colon, rectum, bone, blood, intestine, pancreas, breast, head, neck, lungs, spleen, liver, kidney, brain, thyroid, prostate, urinary bladder, thyroid, skin, abdominal cavity, thoracic cavity, and combinations thereof.

21. The method of claim 18, wherein the cancer is ovarian cancer.

22. The method of claim 18, wherein the cancer is glioma.

23. The method of claim 18, wherein the nucleic acid comprises a polynucleotide encoding a protein selected from the group consisting of interleukin-2, interleukin-4, interleukin-7, interleukin-12, interleukin-15, interferon-α, interferon-β, interferon-γ, colony stimulating factor, granulocyte-macrophage colony stimulating factor, angiogenic agents, clotting factors, hypoglycemic agents, apoptosis factors, anti-angiogenic agents, thymidine kinase, p53, IP10, p16, TNF-α, Fas-ligand, tumor antigens, neuropeptides, viral antigens, bacterial antigens, and combinations thereof.

24. The method of claim 18, wherein the nucleic acid is a plasmid comprising a polynucleotide encoding interleukin-12.

25. The method of claim 18, wherein the ratio of amine nitrogen in the cationic lipopolymer to phosphate in the nucleic acid is from about 0.1:1 to about 100:1.

26. The method of claim 18, wherein the cationic polymer has a molecular weight of from about 50 to about 500,000 Daltons.

27. The method of claim 18, wherein the particle size of the complex remains constant at 4° C. for at least 90 days following reconstitution.

28. The method of claim 18, wherein the reconstituted composition has a nucleic acid concentration of at least 0.5 mg/ml without agglomeration of the nucleic acid.

* * * * *